US007790847B2

(12) United States Patent
Wang et al.

(10) Patent No.: US 7,790,847 B2
(45) Date of Patent: Sep. 7, 2010

(54) GENETICALLY PROGRAMMED EXPRESSION OF PROTEINS CONTAINING THE UNNATURAL AMINO ACID PHENYLSELENOCYSTEINE

(75) Inventors: Jiangyun Wang, La Jolla, CA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 183 days.

(21) Appl. No.: 11/724,039

(22) Filed: Mar. 13, 2007

(65) Prior Publication Data
US 2007/0238152 A1    Oct. 11, 2007

Related U.S. Application Data

(60) Provisional application No. 60/783,272, filed on Mar. 16, 2006, provisional application No. 60/861,456, filed on Nov. 28, 2006.

(51) Int. Cl.
*C07K 14/00* (2006.01)
*C12N 9/00* (2006.01)
*C12N 15/74* (2006.01)
*C07H 21/02* (2006.01)

(52) U.S. Cl. ............... 530/350; 530/300; 435/183; 435/471; 435/488; 536/23.2

(58) Field of Classification Search ............... None
See application file for complete search history.

(56) References Cited

U.S. PATENT DOCUMENTS

| | | | |
|---|---|---|---|
| 6,927,042 | B2 | 8/2005 | Schultz et al. |
| 7,045,337 | B2 | 5/2006 | Schultz et al. |
| 7,083,970 | B2 | 8/2006 | Schultz et al. |
| 7,129,333 | B2 | 10/2006 | Schultz et al. |
| 7,183,082 | B2 | 2/2007 | Schultz et al. |
| 7,199,222 | B2 | 4/2007 | Schultz et al. |
| 7,217,809 | B2 | 5/2007 | Schultz et al. |
| 7,238,510 | B2 | 7/2007 | Schultz et al. |
| 7,262,040 | B2 | 8/2007 | Schultz et al. |
| 2003/0082575 | A1 | 5/2003 | Schultz et al. |
| 2003/0108885 | A1 | 6/2003 | Schultz et al. |
| 2004/0198637 | A1 | 10/2004 | Schultz et al. |
| 2004/0265952 | A1 | 12/2004 | Deiters et al. |
| 2005/0009049 | A1 | 1/2005 | Chin et al. |
| 2005/0136513 | A1 | 6/2005 | Zhang et al. |
| 2005/0208536 | A1 | 9/2005 | Schultz et al. |
| 2005/0227318 | A1 | 10/2005 | Alfonta et al. |
| 2005/0272121 | A1 | 12/2005 | Xie et al. |
| 2005/0287639 | A1 | 12/2005 | Kwon et al. |
| 2006/0063244 | A1 | 3/2006 | Schultz et al. |
| 2006/0068478 | A1 | 3/2006 | Schultz et al. |
| 2006/0073507 | A1 | 4/2006 | Deiters et al. |
| 2006/0110784 | A1 | 5/2006 | Deiters et al. |
| 2006/0110796 | A1 | 5/2006 | Schultz et al. |
| 2006/0134746 | A1 | 6/2006 | Deiters et al. |
| 2006/0160175 | A1 | 7/2006 | Anderson et al. |
| 2006/0177900 | A1 | 8/2006 | Anderson et al. |
| 2006/0234367 | A1 | 10/2006 | Schultz et al. |
| 2006/0246509 | A1 | 11/2006 | Deiters et al. |
| 2007/0009990 | A1 | 1/2007 | Alfonta et al. |
| 2007/0020634 | A1 | 1/2007 | Anderson et al. |
| 2007/0042461 | A1 | 2/2007 | Anderson et al. |
| 2007/0111193 | A1 | 5/2007 | Zhang et al. |
| 2007/0154952 | A1 | 7/2007 | Chin et al. |
| 2007/0166791 | A1 | 7/2007 | Chin et al. |
| 2007/0172915 | A1 | 7/2007 | Schultz et al. |
| 2007/0178448 | A1 | 8/2007 | Tsao et al. |
| 2007/0184517 | A1 | 8/2007 | Schultz et al. |
| 2007/0238152 | A1 | 10/2007 | Wang et al. |

FOREIGN PATENT DOCUMENTS

| | | |
|---|---|---|
| WO | WO 2006/110182 | 12/2006 |
| WO | WO 2007/103490 | 9/2007 |

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Feng et al. (2003) "Expanding tRNA recognition of a tRNA synthetase by a single amino acid change" *Proceedings of the National Academy of Sciences, USA*, 100(10):5676-5681.
Forster et al.,(2003) "Programming peptidomimetic synthetases by translating genetic codes designed de novo." *Proceedings of the National Academy of Sciences, USA*, 100(11): 6353-6357.
Francisco et al. (1993) "Production and fluorescence-activated cell sorting of *Escherichia coli* expressing a functional antibody fragment on the external surface." *Proceedings of the National Academy of Sciences, USA*, 90: 10444-10448.
Hirao et al. (2002) "An unnatural base pair for incorporating amino acid analogues into protein." *Nature Biotechnology*, 20: 177-182.
Liu and Schultz (1999) "Progress toward the evolution of an organism with an expanded genetic code." *Proceedings of the National Academy of Sciences, USA*, 96: 4780-4785.
Wang and Schultz (2005) "Expanding the Genetic Code," *Angewandte Chemie Int. Ed.*, 44(1): 34-66.

(Continued)

*Primary Examiner*—Maria Marvich
(74) *Attorney, Agent, or Firm*—Quine Intellectual Property Law Group; Gary Baker

(57) ABSTRACT

The invention relates to orthogonal pairs of tRNAs and aminoacyl-tRNA synthetases that can incorporate the unnatural amino acid phenylselenocysteine into proteins produced in eubacterial host cells such as *E. coli*. The invention provides, for example but not limited to, novel orthogonal aminoacyl-tRNA synthetases, polynucleotides encoding the novel synthetase molecules, methods for identifying and making the novel synthetases, methods for producing proteins containing the unnatural amino acid phenylselenocysteine and translation systems. The invention further provides methods for producing modified proteins (e.g., lipidated proteins) through targeted modification of the phenylselenocysteine residue in a protein.

16 Claims, 4 Drawing Sheets

OTHER PUBLICATIONS

Wang and Schultz (2002) "Expanding the Genetic Code," *Chem. Commun.*, 1: 1-11.

Wang et. al. (2006) "Expanding the Genetic Code," *Annual Review of Biophysics & Biomolecular Structure*, 35: 225-249.

Wu et al. (2002) "Enzymatic Phosphorylation of Unnatural Nucleosides." *Journal of the American Chemistry Society*, 124: 14626-14630.

Xie and Schultz (2006) "A chemical toolkit for proteins—an expanded genetic code," *Nature Reviews: Molecular Cell Biology*, 7(10): 775-782.

Xie and Schultz (2005) "Adding Amino Acids to the Genetic Repertoire." *Current Opinion in Chemical Biology*, 9(6): 548-554.

Xie and Schultz (2005) "An Expanding Genetic Code," *Methods*, 36(3): 227-238.

* cited by examiner

Nucleotide and Amino Acid Sequences

| SEQ ID NO: | Description | SEQUENCE |
|---|---|---|
| 1 | *Methanococcus jannaschii* - suppressor tyrosyl-tRNA$_{CUA}$ aka *Mj*tRNA-Tyr(CUA) or mutRNA$_{CUA}^{Tyr}$ | CCGGCGGUAGUUCAGCAGGGCAGAACGGCGGACUCUAAAUCCG CAUGGCGCUGGUUCAAAUCCGGCCCGCCGGACCA |
| 2 | Wild-type *Methanococcus jannaschii* tyrosyl-tRNA synthetase (MjTyrRS) amino acid sequence | MDEFEMIKRNTSEIISEEELREVLKKDEKSAYIGFEPSGKIHL GHYLQIKKMIDLQNAGFDIIILLADLHAYLNQKGELDEIRKIG DYNKKVFEAMGLKAKYVYGSEFQLDKDYTLNVYRLALKTTLKR ARRSMELIAREDENPKVAEVIYPIMQVNDIHYLGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 3 | Wild-type *Methanococcus jannaschii* tyrosyl-tRNA synthetase (MjTyrRS) nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTTACATAGGTTTTGAACCAAGTGGTAAAATACATTTA GGGCATTATCTCCAAATAAAAAAGATGATTGATTTACAAAATG CTGGATTTGATATAATTATATTGTTGGCTGATTTACACGCCTA TTTAAACCAGAAAGGAGAGTTGGATGAGATTAGAAAAATAGGA GATTATAACAAAAAAGTTTTTGAAGCAATGGGGTTAAAGGCAA AATATGTTTATGGAAGTGAATTCCAGCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATGA TATTCATTATTTAGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGAGATTA |
| 4 | CLONE 1 (SD) Phenylselenocysteine aminoacyl-tRNA synthetase clone SD (PhSeRS-SD) amino acid sequence (derived from wild-type *Methanococcus jannaschii* tyrosyl tRNA-synthetase) | MDEFEMIKRNTSEIISEEELREVLKKDEKSAWIGFEPSGKIHL GHYLQIKKMIDLQNAGFDIIIELADLGAYLNQKGELDEIRKI GDYNKKVFEAMGLKAKYVYGSEFQLDKDYTLNVYRLALKTTLK RARRSMELIAREDENPKVAEVIYPIMQVNQIHYSGVDVAVGG MEQRKIHMLARELLPKKVVCIHNPVLTGLDGEGKMSSSKGNFI AVDDSPEEIRAKIKKAYCPAGVVEGNPIMEIAKYFLEYPLTIK RPEKFGGDLTVNSYEELESLFKNKELHPMDLKNAVAEELIKIL EPIRKRL |

Fig. 2

| SEQ ID NO: | Description | SEQUENCE |
|---|---|---|
| 5 | CLONE 1 (SD) Phenylselenocysteine aminoacyl-tRNA synthetase clone SD (PhSeRS-SD) nucleotide sequence | ATGGACGAATTTGAAATGATAAAGAGAAACACATCTGAAATTA<br>TCAGCGAGGAAGAGTTAAGAGAGGTTTTAAAAAAAGATGAAAA<br>ATCTGCTTGGATAGGTTTTGAACCAAGTGGTAAAATACATTTA<br>GGGCATTATCTCCAAATAAAAAAGATGATTGATTTACAAAATG<br>CTGGATTTGATATAATTATAGAGTTGGCTGATTTAGGGGCCTA<br>TTTAAACCAGAAAGGAGAGTTGGATGAGATTAGAAAAATAGGA<br>GATTATAACAAAAAAGTTTTTGAAGCAATGGGGTTAAAGGCAA<br>AATATGTTTATGGAAGTGAATTCCAGCTTGATAAGGATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>CAAAGGTTGCTGAAGTTATCTATCCAATAATGCAGGTTAATCA<br>AATTCATTATAGTGGCGTTGATGTTGCAGTTGGAGGGATGGAG<br>CAGAGAAAAATACACATGTTAGCAAGGGAGCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGGGCTAAGATAAAGAAAGCAT<br>ACTGCCCAGCTGGAGTTGTTGAAGGAAATCCAATAATGGAGAT<br>AGCTAAATACTTCCTTGAATATCCTTTAACCATAAAAAGGCCA<br>GAAAAATTTGGTGGAGATTTGACAGTTAATAGCTATGAGGAGT<br>TAGAGAGTTTATTTAAAAATAAGGAATTGCATCCAATGGATTT<br>AAAAAATGCTGTAGCTGAAGAACTTATAAAGATTTTAGAGCCA<br>ATTAGAAAGAGATTATAA |
| 6 | CLONE 2 (K4) Phenylselenocysteine aminoacyl-tRNA synthetase clone K4 (PhSeRS-K4) amino acid sequence (derived from wild-type *Methanococcus jannaschii* tyrosyl tRNA-synthetase) | MDEFEMIKRNTSEIISEEELREVLKKDEKSAWIGFEPSGKIHL<br>GHYLQIKKMIDLQNAGFDIIIHLADLGAYLNQKGELDEIRKI<br>GDYNKKVFEAMGLKAKYVYGSENSLDKDYTLNVYRLALKTTL<br>KRARRSMELIAREDENPKVAEVIYPIMQVNSIHYEGVDVAVG<br>GMEQRKIHMLARELLPKKVVCIHNPVLTGLDGEGKMSSSKGNF<br>IAVDDSPEEIRAKIKKAYCPAGVVEGNPIMEIAKYFLEYPLTI<br>KRPEKFGGDLTVNSYEELESLFKNKELHPMDLKNAVAEELIKI<br>LEPIRKRL |
| 7 | CLONE 2 (K4) Phenylselenocysteine aminoacyl-tRNA synthetase clone K4 (PhSeRS-K4) nucleotide sequence | ATGGACGAATTTGAAATGATAAAGAGAAACACATCTGAAATTA<br>TCAGCGAGGAAGAGTTAAGAGAGGTTTTAAAAAAAGATGAAAA<br>ATCTGCTTGGATAGGTTTTGAACCAAGTGGTAAAATACATTTA<br>GGGCATTATCTCCAAATAAAAAAGATGATTGATTTACAAAATG<br>CTGGATTTGATATAATTATACATTTGGCTGATTTAGGCGCCTA<br>TTTAAACCAGAAAGGAGAGTTGGATGAGATTAGAAAAATAGGA<br>GATTATAACAAAAAAGTTTTTGAAGCAATGGGGTTAAAGGCAA<br>AATATGTTTATGGAAGTGAAAATTCTCTTGATAAGGATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>CAAAGGTTGCTGAAGTTATCTATCCAATAATGCAGGTTAATTC<br>TATTCATTATGAGGGCGTTGATGTTGCAGTTGGAGGGATGGAG<br>CAGAGAAAAATACACATGTTAGCAAGGGAGCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGGGCTAAGATAAAGAAAGCAT<br>ACTGCCCAGCTGGAGTTGTTGAAGGAAATCCAATAATGGAGAT<br>AGCTAAATACTTCCTTGAATATCCTTTAACCATAAAAAGGCCA<br>GAAAAATTTGGTGGAGATTTGACAGTTAATAGCTATGAGGAGT<br>TAGAGAGTTTATTTAAAAATAAGGAATTGCATCCAATGGATTT<br>AAAAAATGCTGTAGCTGAAGAACTTATAAAGATTTTAGAGCCA<br>ATTAGAAAGAGATTATAA |

Fig. 2 (continued)

| SEQ ID NO: | Description | SEQUENCE |
|---|---|---|
| 8 | CLONE 3 (K5) Phenylselenocysteine aminoacyl-tRNA synthetase clone K5 (PhSeRS-K5) amino acid sequence (derived from wild-type *Methanococcus jannaschii* tyrosyl tRNA-synthetase) | MDEFEMIKRNTSEIISEEELREVLKKDEKSAWIGFEPSGKIHL GHYLQIKKMIDLQNAGFDIIHLGDLGAYLNQKGELDEIRKI GDYNKKVFEAMGLKAKYVYGSEKSLDKDYTLNVYRLALKTTL KRARRSMELIAREDENPKVAEVIYPIMQVNEIHYEGVDVAVG GMEQRKIHMLARELLPKKVVCIHNPVLTGLDGEGKMSSSKGNF IAVDDSPEEIRAKIKKAYCPAGVVEGNPIMEIAKYFLEYPLTI KRPEKFGGDLTVNSYEELESLFKNKELHPMDLKNAVAEELIKI LEPIRKRL |
| 9 | CLONE 3 (K5) Phenylselenocysteine aminoacyl-tRNA synthetase clone K5 (PhSeRS-K5) nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTTGGATAGGTTTTGAACCAAGTGGTAAAATACATTTA GGGCATTATCTCCAAATAAAAAAGATGATTGATTTACAAAATG CTGGATTTGATATAATTATACATTTGGGTGATTTAGGCGCCTA TTTAAACCAGAAAGGAGAGTTGGATGAGATTAGAAAAATAGGA GATTATAACAAAAAAGTTTTTGAAGCAATGGGGTTAAAGGCAA AATATGTTTATGGAAGTGAAAAGTCTCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATGA GATTCATTATGAGGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGAGATTATAA |

Fig. 2 (continued)

GENETICALLY PROGRAMMED EXPRESSION OF PROTEINS CONTAINING THE UNNATURAL AMINO ACID PHENYLSELENOCYSTEINE

CROSS-REFERENCE TO RELATED APPLICATIONS

This application claims priority to and benefit of: U.S. Provisional Patent Appl. Ser. No. 60/783,272, filed Mar. 16, 2006; and U.S. Provisional Patent Appl. Ser. No. 60/861,456, filed Nov. 28, 2006, the contents of which are both hereby incorporated by reference in their entirety for all purposes.

STATEMENT AS TO RIGHTS TO INVENTIONS MADE UNDER FEDERALLY SPONSORED RESEARCH AND DEVELOPMENT

A portion of the work described herein was supported by Grant No. GM62159 from the National Institutes of Health, and grant numbers DE FG03 00ER45812 and ER46051 from the Department of Energy. The government has certain rights to this invention.

FIELD OF THE INVENTION

The invention is in the field of translation biochemistry. The invention relates to compositions and methods for making and using orthogonal tRNAs, orthogonal aminoacyl-tRNA synthetases, and pairs thereof, that incorporate unnatural amino acids into proteins. The invention also relates to methods of producing proteins in cells using such pairs and proteins made by the methods.

BACKGROUND OF THE INVENTION

The study of protein structure and function has historically relied upon the properties and reaction chemistries that are available using the reactive groups of the naturally occurring amino acids. Unfortunately, every known organism, from bacteria to humans, encodes the same twenty common amino acids. These 20 amino acids comprise a surprisingly limited number of functional groups: nitrogen bases, carboxylic acids and amides, alcohols, and a thiol group. This limited selection of R-groups has restricted the study of protein structure and function, where the studies are confined by the chemical properties of the naturally occurring amino acids. For example, the limited number of naturally occurring reactive R-groups has limited the ability to make highly targeted protein modifications to the exclusion of the other amino acids in a protein.

Chemoselective ligation reactions involving proteins are extremely important for a variety of purposes, including but not limited to studying protein-protein interaction and cellular signaling, and generating novel protein therapeutics. Most selective protein modification reactions currently used in the art involve covalent bond formation between nucleophilic and electrophilic reaction partners that target naturally occurring nucleophilic residues in the protein amino acid side chains, e.g., the reaction of α-halo ketones with histidine or cysteine side chains. Selectivity in these cases is determined by the number and accessibility of the nucleophilic residues in the protein. Unfortunately, naturally occurring proteins frequently contain poorly positioned (e.g., inaccessible) reaction sites or multiple reaction targets (e.g., lysine, histidine and cysteine residues), resulting in poor selectivity in the modification reactions, making highly targeted protein modification by nucleophilic/electrophilic reagents difficult. Furthermore, the sites of modification are typically limited to the naturally occurring nucleophilic side chains of lysine, histidine or cysteine. Modification at other sites is difficult or impossible.

What is needed in the art are new strategies for incorporation of unnatural amino acids into proteins for the purpose of modifying and studying protein structure and function, where the unnatural amino acids have novel reaction chemistries or other properties, e.g., biological properties not found in the naturally occurring amino acids. There is a considerable need in the art for the creation of new strategies for protein modification reactions that modify proteins in a highly selective fashion, and furthermore, modify proteins under physiological conditions. What is needed in the art are novel methods for producing protein modifications, where the modifications are highly specific, e.g., modifications where none of the naturally occurring amino acids are subject to cross reactions or side reactions. Novel chemistries for highly specific protein modification strategies find a wide variety of applications in the study of protein structure and function and in the production of therapeutic proteins.

Protein Lipidation

Protein lipidation is a key post-translational modification that is involved in protein localization, proper intracellular protein trafficking and protein-protein interactions. Lipidation of proteins is frequently required for proper biological activity. This feature is critical for the development of some therapeutic proteins. Lipidation is also critical in studying protein-protein interactions and cellular signaling. Unfortunately, in vitro chemoselective ligation to produce lipidated proteins using the native unlipidated form of the protein is extremely difficult, and is generally limited to modification of unique surface exposed cysteine residues.

The biological activities of many cellular proteins require association with the cell membrane, which is dependent on the post-translation modification of cysteine by lipid residues such as farnesyl, myristoyl, and palmitoyl moieties (Chernomordik and Kozlov (2003), *Annual Review of Biochemistry* 72:175-207). For example, many G-protein coupled receptors are palmitoylated, Ras proteins are both farnesylated and palmitoylated (Chernomordik and Kozlov (2003), *Annual Review of Biochemistry* 72:175-207). While protein farnesylation is a stable and irreversible modification, palmitoylation is reversible, resulting in dynamic regulation of protein function, and specific targeting to cellular membranes (Rocks et al. (2005), *Science* 307(5716):1746-1752). Furthermore, γ-carboxyglutamic acid is an essential modification that is important for calcium-dependent membrane adhesion in the coagulation cascade (Davie et al. (1991), *Biochemistry* 30(43): 10363-10370).

Orthogonal Translation Systems

One strategy to overcome the limitations of a limited genetic code is to expand the genetic code and add amino acids that have novel reactive properties to the biological repertoire. A general methodology has been developed for the in vivo site-specific incorporation of diverse unnatural amino acids into proteins in both prokaryotic and eukaryotic organisms. These methods rely on orthogonal protein translation components that recognize a suitable selector codon to insert a desired unnatural amino acid at a defined position during polypeptide translation in vivo. These methods utilize an orthogonal tRNA (O-tRNA) that recognizes a selector codon, and where a corresponding specific orthogonal aminoacyl-tRNA synthetase (an O-RS) charges the O-tRNA with the unnatural amino acid. These components do not cross-react with any of the endogenous tRNAs, RSs, amino acids or codons in the host organism (i.e., it must be orthogonal). The use of such orthogonal tRNA-RS pairs has made it possible to genetically encode a large number of structurally diverse unnatural amino acids.

The practice of using orthogonal translation systems that are suitable for making proteins that comprise one or more unnatural amino acid is generally known in the art, as are the general methods for producing orthogonal translation systems. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004 and WO 2006/110182, filed Oct. 27, 2005, entitled "ORTHOGONAL TRANSLATION COMPONENTS FOR THE VIVO INCORPORATION OF UNNATURAL AMINO ACIDS." Each of these applications is incorporated herein by reference in its entirety. For additional discussion of orthogonal translation systems that incorporate unnatural amino acids, and methods for their production and use, see also, Wang and Schultz, "Expanding the Genetic Code," *Chem. Commun.* (*Camb.*) 1:1-11 (2002); Wang and Schultz "Expanding the Genetic Code," *Angewandte Chemie Int. Ed.,* 44(1):34-66 (2005); Xie and Schultz, "An Expanding Genetic Code," *Methods* 36(3):227-238 (2005); Xie and Schultz, "Adding Amino Acids to the Genetic Repertoire," *Curr. Opinion in Chemical Biology* 9(6):548-554 (2005); Wang et al., "Expanding the Genetic Code," *Annu. Rev. Biophys. Biomol. Struct.,* 35:225-249 (2006); and Xie and Schultz, "A Chemical Toolkit for Proteins—an Expanded Genetic Code," *Nat. Rev. Mol. Cell Biol.,* 7(10):775-782 (2006).

There is a need in the art for the development of orthogonal translation components that incorporate unnatural amino acids into proteins, where the unnatural amino acids can be incorporated at a defined position, and where the unnatural amino acids have novel chemical properties that allow the amino acid to serve as a target for specific modification (e.g., lipidation) to the exclusion of cross reactions or side reactions with other sites in the proteins. The invention described herein fulfills these and other needs, as will be apparent upon review of the following disclosure.

SUMMARY OF THE INVENTION

The invention provides compositions and methods for incorporating the unnatural amino acid phenylselenocysteine into a growing polypeptide chain in response to a selector codon, e.g., an amber stop codon, in vivo (e.g., in a host cell). These compositions include pairs of orthogonal-tRNAs (O-tRNAs) and orthogonal aminoacyl-tRNA synthetases (O-RSs) that do not interact with the host cell translation machinery. That is to say, the O-tRNA is not charged (or not charged to a significant level) with an amino acid (natural or unnatural) by an endogenous host cell aminoacyl-tRNA synthetase. Similarly, the O-RSs provided by the invention do not charge any endogenous tRNA with an amino acid (natural or unnatural) to a significant or in some cases detectable level. These novel compositions permit the production of large quantities of proteins having translationally incorporated unnatural amino acids. The chemical properties of the phenylselenocysteine unnatural amino acid also permit the targeted modification of that residue to produce desired conjugations, for example but not limited to, lipid conjugations. Such specifically modified polypeptides can find use as therapeutics and in biomedical research.

In some aspects, the invention provides translation systems. These systems comprise a first orthogonal aminoacyl-tRNA synthetase (O-RS), a first orthogonal tRNA (O-tRNA), and a first unnatural amino acid that is phenylselenocysteine, where the first O-RS preferentially aminoacylates the first O-tRNA with the first unnatural amino acid phenylselenocysteine. In some aspects, the O-RS preferentially aminoacylates the O-tRNA with said phenylselenocysteine with an efficiency that is at least 50% of the efficiency observed for a translation system comprising that same O-tRNA, the phenylselenocysteine, and an aminoacyl-tRNA synthetase comprising the amino acid sequence of SEQ ID NO: 4, 6 or 8.

The translation systems can use components derived from a variety of sources. In one embodiment, the O-RS used in the system can comprise the amino acid sequence of SEQ ID NOS: 4, 6 or 8, and conservative variants of that sequence. In some embodiments, the O-tRNA is an amber suppressor tRNA. In some embodiments, the O-tRNA comprises or is encoded by SEQ ID NO: 1.

In some aspects, the translation system further comprises a nucleic acid encoding a protein of interest, where the nucleic acid has at least one selector codon that is recognized by the O-tRNA.

In some aspects, the translation system incorporates a second orthogonal pair (that is, a second O-RS and a second O-tRNA) that utilizes a second unnatural amino acid, so that the system is now able to incorporate at least two different unnatural amino acids at different selected sites in a polypeptide. In this dual system, the second O-RS preferentially aminoacylates the second O-tRNA with a second unnatural amino acid that is different from the first unnatural amino acid, and the second O-tRNA recognizes a selector codon that is different from the selector codon recognized by the first O-tRNA.

In some embodiments, the translation system resides in a host cell (and includes the host cell). The host cell used in not particularly limited, as long as the O-RS and O-tRNA retain their orthogonality in their host cell environment. The host cell can be a eubacterial cell, such as *E. coli.* The host cell can comprise one or more polynucleotides that encode components of the translation system, including the O-RS or O-tRNA. In some embodiments, the polynucleotide encoding the O-RS comprises a nucleotide sequence of SEQ ID NO: 5, 7 or 9.

The invention also provides methods for producing proteins having one or more unnatural amino acids at selected positions. These methods utilize the translation systems described above. Generally, these methods start with the step of providing a translation system comprising: (i) a first unnatural amino acid that is phenylselenocysteine; (ii) a first orthogonal aminoacyl-tRNA synthetase (O-RS); (iii) a first orthogonal tRNA (O-tRNA), wherein the O-RS preferentially aminoacylates the O-tRNA with the unnatural amino acid; and, (iv) a nucleic acid encoding the protein, where the nucleic acid comprises at least one selector codon (optionally an amber codon) that is recognized by the first O-tRNA. The method then incorporates the unnatural amino acid at the selected position in the protein during translation of the protein in response to the selector codon, thereby producing the protein comprising the unnatural amino acid at the selected position. In some aspects of these methods, the O-RS preferentially aminoacylates the O-tRNA with the phenylselenocysteine with an efficiency that is at least 50% of the efficiency observed for a translation system comprising that same O-tRNA, the phenylselenocysteine, and an aminoacyl-tRNA synthetase comprising the amino acid sequence of SEQ ID NO: 4, 6 or 8. In some aspects, the translation system includes a nucleic acid that encodes the O-RS.

These methods can be widely applied using a variety of reagents. In some embodiments, a polynucleotide encoding the O-RS is provided. In some embodiments, the O-RS comprises an amino acid sequence of SEQ ID NO: 4, 6 or 8, or conservative variants thereof. Optionally, the translation system used in the methods includes a nucleic acid that encodes the O-RS, for example, a nucleic acid of SEQ ID NO: 5, 7 or 9.

In some embodiments of these methods, the providing a translation system step comprises mutating an amino acid binding pocket of a wild-type aminoacyl-tRNA synthetase by site-directed mutagenesis, and selecting a resulting O-RS that preferentially aminoacylates the O-tRNA with the unnatural amino acid. The selecting step can comprises positively selecting and negatively selecting for the O-RS from a pool of resulting aminoacyl-tRNA synthetase molecules following site-directed mutagenesis. In some embodiments, the providing step furnishes a polynucleotide encoding the O-tRNA, e.g., an O-tRNA that is an amber suppressor tRNA, or an O-tRNA that comprises or is encoded by a polynucleotide of SEQ ID NO: 1. In these methods, the providing step can also furnish a nucleic acid comprising an amber selector codon that is utilized by the translation system.

These methods can also be modified to incorporate more than one unnatural amino acid into a protein. In those methods, a second orthogonal translation system is employed in conjunction with the first translation system, where the second system has different amino acid and selector codon specificities. For example, the providing step can include providing a second O-RS and a second O-tRNA, where the second O-RS preferentially aminoacylates the second O-tRNA with a second unnatural amino acid that is different from the first unnatural amino acid, and where the second O-tRNA recognizes a selector codon in the nucleic acid that is different from the selector codon recognized by the first O-tRNA.

The methods for producing a protein with an unnatural amino acid can also be conducted in the context of a host cell. In these cases, a host cell is provided, where the host cell comprises the unnatural amino acid, the O-RS, the O-tRNA and the nucleic acid with at least one selector codon that encodes the protein, and where culturing the host cell results in incorporating the unnatural amino acid. In some embodiments, the providing step comprises providing a eubacterial host cell (e.g., *E. coli*). In some embodiments, the providing step includes providing a host cell that contains a polynucleotide encoding the O-RS. For example, the polynucleotide encoding the O-RS can comprise a nucleotide sequence of SEQ ID NO: 5, 7 or 9.

In some variations of these methods, the procedures further include modification of the phenylselenocysteine following its incorporation into a polypeptide. For example, the phenylselenocysteine can be reacted under certain conditions that results in conversion to dehydroalanine at the selected position. This reaction can be by oxidative elimination. The reaction can be carried out by exposing the phenylselenocysteine to hydrogen peroxide.

The invention also provides methods for producing lipidated proteins, where the lipid is conjugated at a designated selected position. These methods utilize the translation systems described above. Generally, these methods start with the step of providing a translation system comprising: (i) a phenylselenocysteine unnatural amino acid; (ii) an orthogonal aminoacyl-tRNA synthetase (O-RS); (iii) an orthogonal tRNA (O-tRNA), where the O-RS preferentially aminoacylates the O-tRNA with the phenylselenocysteine; and, (iv) a nucleic acid encoding the protein, where the nucleic acid comprises at least one selector codon (optionally an amber codon) that is recognized by the O-tRNA. The method then incorporates the phenylselenocysteine at the selected position in the protein during translation of the protein in response to the selector codon. That phenylselenocysteine is then reacted to produce dehydroalanine at the selected position, which is in turn itself reacted with a lipid to produce a lipidated amino acid moiety, thereby producing a protein having a lipid at the selected position in the protein.

In some aspects of these methods, reacting the phenylselenocysteine is by oxidative elimination or exposure to hydrogen peroxide. In some aspects, the conjugated lipid reacted with the dehydroalanine can be thiopalmitic acid, farnesylmercaptan or 1-hexadecanethiol. The lipidated amino acids thus formed are palmitoylcysteine, farnesylcysteine and S-hexadecylcysteine. Modification of the dehydroalanine is typically by a Michael Addition reaction.

The invention also provides methods for producing a protein having a dehydroalanine residue at a selected position. These methods utilize the translation systems described above. Generally, these methods start with the step of providing a translation system comprising: (i) a phenylselenocysteine unnatural amino acid; (ii) an orthogonal aminoacyl-tRNA synthetase (O-RS); (iii) an orthogonal tRNA (O-tRNA), where the O-RS preferentially aminoacylates the O-tRNA with the phenylselenocysteine; and, (iv) a nucleic acid encoding the protein, where the nucleic acid comprises at least one selector codon (optionally an amber codon) that is recognized by the O-tRNA. The method then incorporates the phenylselenocysteine at the selected position in the protein during translation of the protein in response to the selector codon. That phenylselenocysteine is then reacted to produce dehydroalanine at the selected position. In some aspects of these methods, reacting the phenylselenocysteine is by oxidative elimination or exposure to hydrogen peroxide.

The invention also provides a variety of compositions, including nucleic acids and proteins. The nature of the composition is not particularly limited, other than the composition comprises the specified nucleic acid or protein. The compositions of the invention can comprise any number of additional components of any nature.

For example, the invention provides compositions comprising O-RS polypeptides, where the polypeptides comprise the amino acid sequence of SEQ ID NO: 4, 6 or 8, or a conservative variant thereof. In some aspects, the conservative variant polypeptide aminoacylates a cognate orthogonal tRNA (O-tRNA) with an unnatural amino acid with an efficiency that is at least 50% of the efficiency observed for a translation system comprising the O-tRNA, the unnatural amino acid, and an aminoacyl-tRNA synthetase comprising the amino acid sequence of SEQ ID NO: 4, 6, 8 or 10. The invention also provides polynucleotides that encode any of these polypeptides above. In some embodiments, these polynucleotides can comprise a nucleotide sequence of SEQ ID NO: 5, 7 or 9. In some embodiments, the polypeptides are in a cell.

The invention also provides polynucleotide compositions comprising a nucleotide sequence of SEQ ID NO: 5, 7 or 9. In some embodiments, the invention provides vectors comprising the polynucleotides, e.g., expression vectors. In some embodiments, the invention provides cells comprising a vector described above.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes combinations of two or more cells; reference to "a polynucleotide" includes, as a practical matter, many copies of that polynucleotide.

Unless defined herein and below in the reminder of the specification, all technical and scientific terms used herein have the same meaning as commonly understood by one of ordinary skill in the art to which the invention pertains.

Orthogonal: As used herein, the term "orthogonal" refers to a molecule (e.g., an orthogonal tRNA (O-tRNA) and/or an orthogonal aminoacyl-tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding tRNA/RS endogenous pair, or an active orthogonal pair (e.g., a tyrosyl orthogonal tRNA/RS pair).

Orthogonal tyrosyl-tRNA: As used herein, an orthogonal tyrosyl-tRNA (tyrosyl-O-tRNA) is a tRNA that is orthogonal to a translation system of interest, where the tRNA is: (1) identical or substantially similar to a naturally occurring tyrosyl-tRNA, (2) derived from a naturally occurring tyrosyl-tRNA by natural or artificial mutagenesis, (3) derived by any process that takes a sequence of a wild-type or mutant tyrosyl-tRNA sequence of (1) or (2) into account, (4) homologous to a wild-type or mutant tyrosyl-tRNA; (5) homologous to any example tRNA that is designated as a substrate for a tyrosyl-tRNA synthetase in FIG. 2, or (6) a conservative variant of any example tRNA that is designated as a substrate for a tyrosyl-tRNA synthetase in FIG. 2. The tyrosyl-tRNA can exist charged with an amino acid, or in an uncharged state. It is also to be understood that a "tyrosyl-O-tRNA" optionally is charged (aminoacylated) by a cognate synthetase with an amino acid other than tyrosine, respectively, e.g., with an unnatural amino acid. Indeed, it will be appreciated that a tyrosyl-O-tRNA of the invention is advantageously used to insert essentially any amino acid, whether natural or unnatural, into a growing polypeptide, during translation, in response to a selector codon.

Orthogonal tyrosyl amino acid synthetase: As used herein, an orthogonal tyrosyl amino acid synthetase (tyrosyl-O-RS) is an enzyme that preferentially aminoacylates the tyrosyl-O-tRNA with an amino acid in a translation system of interest. The amino acid that the tyrosyl-O-RS loads onto the tyrosyl-O-tRNA can be any amino acid, whether natural, unnatural or artificial, and is not limited herein. The synthetase is optionally the same as or homologous to a naturally occurring tyrosyl amino acid synthetase, or the same as or homologous to a synthetase designated as an O-RS in FIG. 2. For example, the O-RS can be a conservative variant of a tyrosyl-O-RS of FIG. 2, and/or can be at least 50%, 60%, 70%, 80%, 90%, 95%, 98%, 99% or more identical in sequence to an O-RS of FIG. 2.

Cognate: The term "cognate" refers to components that function together, or have some aspect of specificity for each other, e.g., an orthogonal tRNA and an orthogonal aminoacyl-tRNA synthetase. The components can also be referred to as being complementary.

Preferentially aminoacylates: As used herein in reference to orthogonal translation systems, an O-RS "preferentially aminoacylates" a cognate O-tRNA when the O-RS charges the O-tRNA with an amino acid more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O-RS "preferentially aminoacylates an O-tRNA with an unnatural amino acid" when (a) the O-RS preferentially aminoacylates the O-tRNA compared to an endogenous tRNA, and (b) where that aminoacylation is specific for the unnatural amino acid, as compared to aminoacylation of the O-tRNA by the O-RS with any natural amino acid. That is, when the unnatural and natural amino acids are present in equal molar amounts in a translation system comprising the O-RS and O-tRNA, the O-RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O-RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, typically by allowing the incorporation of an amino acid in response to a stop codon (i.e., "read-through") during the translation of a polypeptide. In some aspects, a selector codon of the invention is a suppressor codon, e.g., a stop codon (e.g., an amber, ocher or opal codon), a four base codon, a rare codon, etc.

Suppression activity: As used herein, the term "suppression activity" refers, in general, to the ability of a tRNA (e.g., a suppressor tRNA) to allow translational read-through of a codon (e.g., a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor tRNA, or as compared to a control system, e.g., a control system lacking an O-RS.

The present invention provides various methods by which suppression activity can be quantitated. Percent suppression of a particular O-tRNA and O-RS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O-RS and an O-tRNA, as compared to a positive control construct, where the positive control lacks the O-tRNA, the O-RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O-RS. Typically, the translation system expressing the test marker also includes an amino acid that is recognized by the O-RS and O-tRNA. Optionally, the percent suppression measurement can be refined by comparison of the test marker to a "background" or "negative" control marker construct, which includes the same selector codon as the test marker, but in a system that does not include the O-tRNA, O-RS and/or relevant amino acid recognized by the O-tRNA and/or O-RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatived lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Translation system: The term "translation system" refers to the components that incorporate an amino acid into a growing polypeptide chain (protein). Components of a translation system can include, e.g., ribosomes, tRNAs, synthetases, mRNA and the like. The O-tRNA and/or the O-RSs of the invention can be added to or be part of an in vitro or in vivo translation system, e.g., in a non-eukaryotic cell, e.g., a bacterium (such as E. coli), or in a eukaryotic cell, e.g., a yeast cell, a mammalian cell, a plant cell, an algae cell, a fungus cell, an insect cell, and/or the like.

Unnatural amino acid: As used herein, the term "unnatural amino acid" refers to any amino acid, modified amino acid, and/or amino acid analogue, that is not one of the 20 common naturally occurring amino acids. For example, the unnatural amino acid phenylselenocysteine (see FIG. 1, structure 1) finds use with the invention.

Derived from: As used herein, the term "derived from" refers to a component that is isolated from or made using a specified molecule or organism, or information from the specified molecule or organism. For example, a polypeptide that is derived from a second polypeptide can include an amino acid sequence that is identical or substantially similar to the amino acid sequence of the second polypeptide. In the case of polypeptides, the derived species can be obtained by, for example, naturally occurring mutagenesis, artificial directed mutagenesis or artificial random mutagenesis. The mutagenesis used to derive polypeptides can be intentionally directed or intentionally random, or a mixture of each. The mutagenesis of a polypeptide to create a different polypeptide derived from the first can be a random event (e.g., caused by polymerase infidelity) and the identification of the derived polypeptide can be made by appropriate screening methods, e.g., as discussed herein. Mutagenesis of a polypeptide typically entails manipulation of the polynucleotide that encodes the polypeptide.

Positive selection or screening marker: As used herein, the term "positive selection or screening marker" refers to a marker that, when present, e.g., expressed, activated or the like, results in identification of a cell, which comprises the trait, e.g., a cell with the positive selection marker, from those without the trait.

Negative selection or screening marker: As used herein, the term "negative selection or screening marker" refers to a marker that, when present, e.g., expressed, activated, or the like, allows identification of a cell that does not comprise a selected property or trait (e.g., as compared to a cell that does possess the property or trait).

Reporter: As used herein, the term "reporter" refers to a component that can be used to identify and/or select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGFP, RFP, etc.), a luminescent marker (e.g., a firefly luciferase protein), an affinity based screening marker, or positive or negative selectable marker genes such as lacZ, β-gal/lacZ (β-galactosidase), ADH (alcohol dehydrogenase), his3, ura3, leu2, lys2, or the like.

Eukaryote: As used herein, the term "eukaryote" refers to organisms belonging to the Kingdom Eucarya. Eukaryotes are generally distinguishable from prokaryotes by their typically multicellular organization (but not exclusively multicellular, for example, yeast), the presence of a membrane-bound nucleus and other membrane-bound organelles, linear genetic material (i.e., linear chromosomes), the absence of operons, the presence of introns, message capping and poly-A mRNA, and other biochemical characteristics, such as a distinguishing ribosomal structure. Eukaryotic organisms include, for example, animals (e.g., mammals, insects, reptiles, birds, etc.), ciliates, plants (e.g., monocots, dicots, algae, etc.), fungi, yeasts, flagellates, microsporidia, protists, etc.

Prokaryote: As used herein, the term "prokaryote" refers to organisms belonging to the Kingdom Monera (also termed Procarya). Prokaryotic organisms are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and mycoplasma are sometimes given separate classifications under the Kingdom Monera.

Bacteria: As used herein, the terms "bacteria" and "eubacteria" refer to prokaryotic organisms that are distinguishable from Archaea. Similarly, Archaea refers to prokaryotes that are distinguishable from eubacteria. Eubacteria and Archaea can be distinguished by a number morphological and biochemical criteria. For example, differences in ribosomal RNA sequences, RNA polymerase structure, the presence or absence of introns, antibiotic sensitivity, the presence or absence of cell wall peptidoglycans adn other cell wall components, the branched versus unbranched structures of membrane lipids, and the presence/absence of histones and histone-like proteins are used to assign an organism to Eubacteria or Archaea.

Examples of Eubacteria include *Escherichia coli, Thermus thermophilus, Bacillus subtilis* and *Bacillus stearothermophilus*. Example of Archaea include *Methanococcus jannaschii* (Mj), *Methanosarcina mazei* (Mm), *Methanobacterium thermoautotrophicum* (Mt), *Methanococcus maripaludis, Methanopyrus kandleri, Halobacterium* such as *Haloferax volcanii* and *Halobacterium* species NRC-1, *Archaeoglobus fulgidus* (Af), *Pyrococcus furiosus* (Pf), *Pyrococcus horikoshii* (Ph), *Pyrobaculum aerophilum, Pyrococcus abyssi, Sulfolobus solfataricus* (Ss), *Sulfolobus tokodaii, Aeuropyrum pernix* (Ap), *Thermoplasma acidophilum* and *Thermoplasma volcanium*.

Conservative variant: As used herein, the term "conservative variant," in the context of a translation component, refers to a translation component, e.g., a conservative variant O-tRNA or a conservative variant O-RS, that functionally performs similar to a base component that the conservative variant is similar to, e.g., an O-tRNA or O-RS, having variations in the sequence as compared to a reference O-tRNA or O-RS. For example, an O-RS, or a conservative variant of that O-RS, will aminoacylate a cognate O-tRNA with a phenylselenocysteine unnatural amino acid. In this example, the O-RS and the conservative variant O-RS do not have the same amino acid sequences. The conservative variant can have, e.g., one variation, two variations, three variations, four variations, or five or more variations in sequence, as long as the conservative variant is still complementary to (e.g., functions with) the cognate corresponding O-tRNA or O-RS.

In some embodiments, a conservative variant O-RS comprises one or more conservative amino acid substitutions compared to the O-RS from which it was derived. In some embodiments, a conservative variant O-RS comprises one or more conservative amino acid substitutions compared to the O-RS from which it was derived, and furthermore, retains O-RS biological activity; for example, a conservative variant O-RS that retains at least 10% of the biological activity of the parent O-RS molecule from which it was derived, or alternatively, at least 20%, at least 30%, or at least 40%. In some preferred embodiments, the conservative variant O-RS retains at least 50% of the biological activity of the parent O-RS molecule from which it was derived. The conservative amino acid substitutions of a conservative variant O-RS can occur in any domain of the O-RS, including the amino acid binding pocket.

Selection or screening agent: As used herein, the term "selection or screening agent" refers to an agent that, when present, allows for selection/screening of certain components from a population. For example, a selection or screening agent can be, but is not limited to, e.g., a nutrient, an antibiotic, a wavelength of light, an antibody, an expressed polynucleotide, or the like. The selection agent can be varied, e.g., by concentration, intensity, etc.

In response to: As used herein, the term "in response to" refers to the process in which an O-tRNA of the invention recognizes a selector codon and mediates the incorporation of the unnatural amino acid, which is coupled to the tRNA, into the growing polypeptide chain.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

BRIEF DESCRIPTION OF THE FIGURES

FIG. 2 provides various nucleotide and amino acid sequences finding use with the invention.

DETAILED DESCRIPTION OF THE INVENTION

Figure 1:
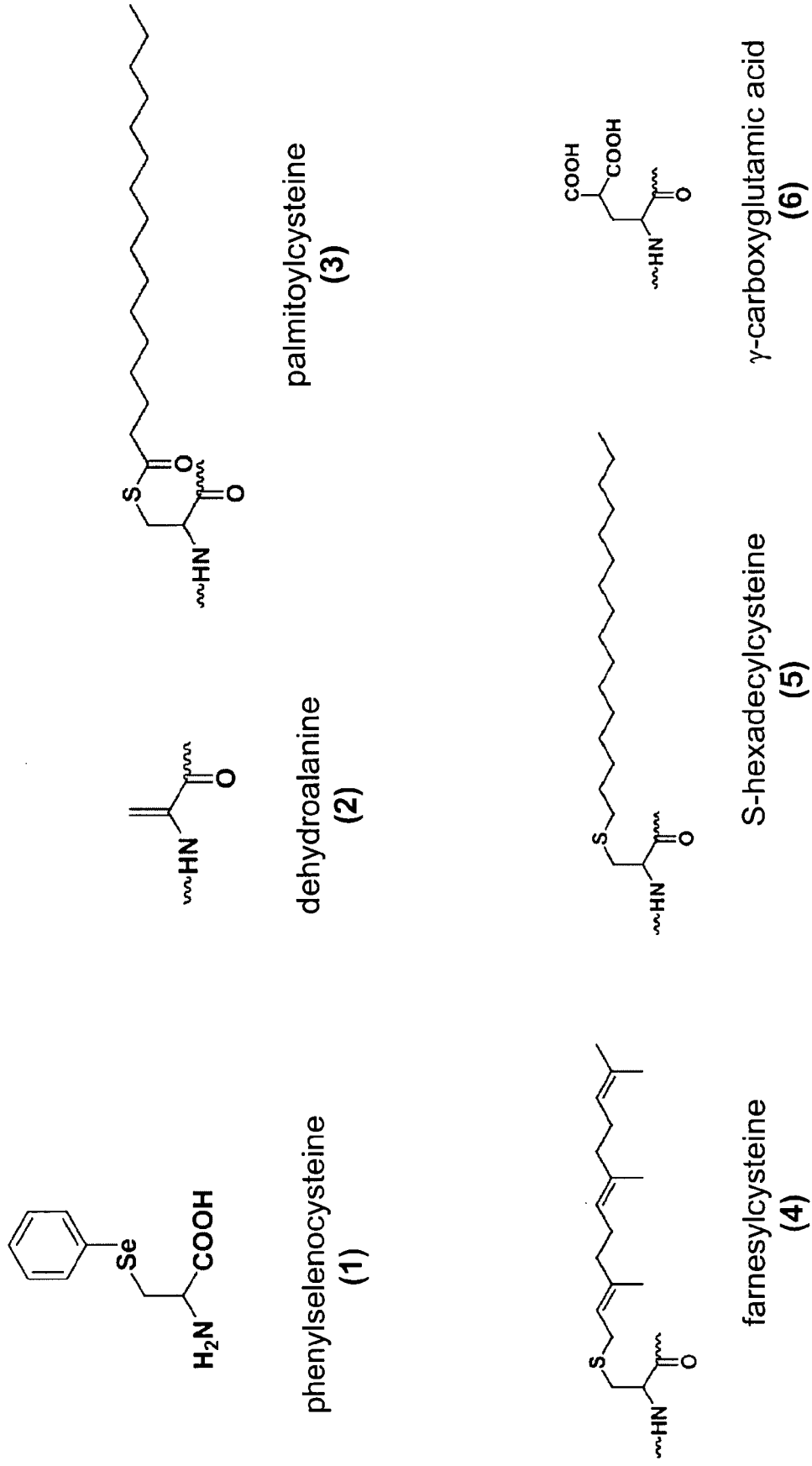
FIG. 1 provides the chemical structures of the unnatural amino acid phenylselenocysteine (structure 1) as well as structures that can be derived from phenylselenocysteine. These structures include dehydroalanine (2), palmitoylcysteine (3), farnesylcysteine (4), S-hexadecylcysteine (5), and gamma-carboxyglutamic acid (6).

The invention provides solutions to the inherent limitations of using a translation system confined by the 20 naturally occurring amino acids. The solutions include compositions and methods related to the programmed, site-specific biosynthetic incorporation of the unnatural amino acid phenylselenocysteine (FIG. 1, structure 1) into proteins using orthogonal translation systems. The incorporation of phenylselenocysteine into the protein can be programmed to occur at any desired position by engineering the polynucleotide encoding the protein of interest to contain a selector codon that signals the incorporation of the unnatural amino acid into the growing polypeptide chain.

The invention provides novel compositions including novel aminoacyl-tRNA synthetases (O-RS) that have the ability to charge a suitable cognate suppressor O-tRNA (e.g., the O-tRNA of SEQ ID NO: 1) with phenylselenocysteine. These O-RS are novel mutants of the *Methanococcus jannaschii* tyrosyl-tRNA synthetase that selectively charge the O-tRNA with the unnatural amino acid phenylselenocysteine in bacterial host cells. Most preferably, the orthogonal components do not cross-react with endogenous host components of the translational machinery of the host cell (e.g., an *E. coli* cell).

The O-RS of the invention can include the O-RS of SEQ ID NOS: 4, 6 or 8. The invention also provides polynucleotides that encode these O-RS polypeptides. The present disclosure also describes the methodology for evolution of the novel O-tRNA/O-RS pairs that function in eubacteria to site-specifically incorporate a phenylselenocysteine unnatural amino acid in response to selector codons.

The invention also provides methods for the highly efficient and site-specific genetic incorporation of phenylselenocysteine (FIG. 1, structure 1) into proteins (preferably in vivo) in response to a selector codon (e.g., the amber nonsense codon, TAG). These novel methods and compositions can be used in, for example, a bacterial host system.

In some cases, the phenylselenocysteine unnatural amino acid can then be specifically and regioselectively modified after its incorporation into a polypeptide, as described in the present disclosure. Because of the reaction chemistry of the phenylseleno-group, proteins into which the unnatural amino acid is incorporated can be modified with extremely high selectivity. In some cases, the phenylselenocysteine unnatural amino acid reactive group has the advantage of being completely alien to in vivo systems, thereby improving reaction selectivity. In some aspects, the modification reactions can be conducted using relatively mild reaction conditions that permit both in vitro and in vivo conjugation reactions involving proteins, and preserving host cell viability and/or protein biological activity.

In some aspects, the incorporated phenylselenocysteine moiety is modified, and that modified product is then in turn again modified, for example, by a conjugation reaction.

The nature of the material that is ultimately conjugated at the selected position in the protein (corresponding to the selector codon in the open reading frame encoding the protein) is not particularly limited, and can be any desired entity, e.g., lipids, dyes, fluorophores, crosslinking agents, saccharide derivatives, polymers (e.g., derivatives of polyethylene glycol), photocrosslinkers, cytotoxic compounds, affinity labels, derivatives of biotin, resins, beads, a second protein or polypeptide (or more), polynucleotide(s) (e.g., DNA, RNA, etc.), metal chelators, cofactors, fatty acids, carbohydrates, and the like.

In some aspects, to demonstrate (but not to limit) the present invention, the disclosure herein describes the phenylselenocysteine unnatural amino acid moiety incorporated into a model protein, for example, myoglobin, human growth hormone and GFP. It is not intended that the incorporation of the phenylselenocysteine unnatural amino acid be limited to any particular protein. It will be clear that the incorporation of phenylselenocysteine unnatural amino acid into any desired protein of interest can be accomplished using the guidance of the present disclosure. Generation of proteins comprising one or more phenylselenocysteine unnatural amino acid (either alone or in combination with other different unnatural amino acids) is advantageous for a variety of purposes, for example, for use in therapeutic proteins and for research purposes.

Modification of Phenylselenocysteine

In some aspects, the invention provides methods for the modification of the phenylselenocysteine amino acid residue following its incorporation into a polypeptide. One such modification, for example, oxidative cleavage, can beneficially convert the phenylselenocysteine amino acid residue into the α,β-unsaturated amino acid dehydroalanine (see FIG. 1, structure 2). This dehydroalanine unnatural amino acid is also reactive and can be subsequently modified.

It is not intended that the invention be limited to any particular mechanism (e.g., oxidative elimination) or specific reaction conditions (for example, exposure to hydrogen peroxide) for the conversion of phenylselenocysteine to dehydroalanine. One of ordinary skill in the art will recognize a variety of suitable alternative mechanisms and reaction conditions that find equal use with the invention for the conversion of a phenylselenocysteine residue to dehydroalanine.

Modification of Dehydroalanine

In some aspects, the invention provides methods for the further modification of a dehydroalanine unnatural amino acid residue in a polypeptide. The dehydroalanine residue is reactive and can be targeted in highly specific modification reactions. These methods are especially useful in forming lipid conjugates to produce lipidated proteins.

As described herein, Michael Addition reactions of the unnatural amino acid dehydroalanine result in proteins having programmed, site-specific post-translational modifications. For example, reaction of dehydroalanine with a thiolipid can generate a lipidated protein. For example, reaction with thiopalmitic acid results in palmitoylcysteine (see FIG. 1, structure 3), reaction with farnesylmercaptan produces farnesylcysteine (see FIG. 1, structure 4), and reaction with malonate produces γ-carboxyglutamic acid (see FIG. 1, structure 6). In addition, reaction with 1-hexadecanethiol results in S-hexadecylcysteine (see FIG. 1, structure 5).

Although the present specification provides these examples, it is not intended that the invention be limited to any particular mechanism (e.g., a Michael Addition pathway) or specific reagents (thio-lipids) in the modification (conjugation) of dehydroalanine. One of ordinary skill in the art will recognize a variety of suitable alternative mechanisms, reaction conditions and reagents that find equal use with the invention for the modification of the dehydroalanine residue. Indeed, modification of the dehydroalanine residue is not limited to lipid conjugation, and this conjugation mechanism can be used to conjugate any desired moiety to the polypeptide at the site of the dehydroalanine.

Orthogonal tRNA/Aminoacyl-tRNA Synthetase Technology

An understanding of the novel compositions and methods of the present invention requires an understanding of the activities associated with orthogonal tRNA and orthogonal aminoacyl-tRNA synthetase pairs. In order to add additional unnatural amino acids to the genetic code, new orthogonal pairs comprising an aminoacyl-tRNA synthetase and a suitable tRNA are needed that can function efficiently in the host translational machinery, but that are "orthogonal" to the translation system at issue, meaning that it functions independently of the synthetases and tRNAs endogenous to the translation system. Desired characteristics of the orthogonal pair include tRNA that decode or recognize only a specific codon, e.g., a selector codon, that is not decoded by any endogenous tRNA, and aminoacyl-tRNA synthetases that preferentially aminoacylate (or "charge") its cognate tRNA with only one specific unnatural amino acid. The O-tRNA is also not typically aminoacylated (or is poorly aminoacylated, i.e., charged) by endogenous synthetases. For example, in an $E.\ coli$ host system, an orthogonal pair will include an aminoacyl-tRNA synthetase that does not cross-react with any of the endogenous tRNA, e.g., which there are 40 in $E.\ coli$, and an orthogonal tRNA that is not aminoacylated by any of the endogenous synthetases, e.g., of which there are 21 in $E.\ coli$.

The general principles of orthogonal translation systems that are suitable for making proteins that comprise one or more unnatural amino acid are known in the art, as are the general methods for producing orthogonal translation systems. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004; and WO 2006/110182, filed on Oct. 27, 2005, entitled "ORTHOGONAL TRANSLATION COMPONENTS FOR THE IN VIVO INCORPORATION OF UNNATURAL AMINO ACIDS." Each of these publications is incorporated herein by reference in their entirety. For discussion of orthogonal translation systems that incorporate unnatural amino acids, and methods for their production and use, see also, Wang and Schultz "Expanding the Genetic Code," *Angewandte Chemie Int. Ed.*, 44(1):34-66 (2005), Xie and Schultz, "An Expanding Genetic Code," *Methods* 36(3):227-238 (2005); Xie and Schultz, "Adding Amino Acids to the Genetic Repertoire," *Curr. Opinion in Chemical Biology* 9(6):548-554 (2005); Wang et al., "Expanding the Genetic Code," *Annu. Rev. Biophys. Biomol. Struct.*, 35:225-249 (2006); and Ryu and Schultz, "Efficient Incorporation of Unnatural Amino Acids into Proteins in *Escherichia coli*," *Nat. Methods* (4):263-265 (2006); the contents of which are each incorporated by reference in their entirety.

Orthogonal Translation Systems

Orthogonal translation systems generally comprise cells (which can be prokaryotic cells such as *E. coli*) that include an orthogonal tRNA (O-tRNA), an orthogonal aminoacyl tRNA synthetase (O-RS), and an unnatural amino acid, where the O-RS aminoacylates the O-tRNA with the unnatural amino acid. An orthogonal pair of the invention can include an O-tRNA, e.g., a suppressor tRNA, a frameshift tRNA, or the like, and a cognate O-RS. The orthogonal systems of the invention can typically comprise O-tRNA/O-RS pairs, either in the context of a host cell or without the host cell. In addition to multi-component systems, the invention also provides novel individual components, for example, novel orthogonal aminoacyl-tRNA synthetase polypeptides (e.g., SEQ ID NO: 4, 6 or 8), and the polynucleotides that encodes those polypeptides (e.g., SEQ ID NO: 5, 7 or 9).

In general, when an orthogonal pair recognizes a selector codon and loads an amino acid in response to the selector codon, the orthogonal pair is said to "suppress" the selector codon. That is, a selector codon that is not recognized by the translation system's (e.g., the cell's) endogenous machinery is not ordinarily charged, which results in blocking production of a polypeptide that would otherwise be translated from the nucleic acid. In an orthogonal pair system, the O-RS aminoacylates the O-tRNA with a specific unnatural amino acid. The charged O-tRNA recognizes the selector codon and suppresses the translational block caused by the selector codon.

In some aspects, an O-tRNA of the invention recognizes a selector codon and includes at least about, e.g., a 45%, a 50%, a 60%, a 75%, a 80%, or a 90% or more suppression efficiency in the presence of a cognate synthetase in response to a selector codon as compared to the suppression efficiency of an O-tRNA comprising or encoded by a polynucleotide sequence as set forth in the sequence listing herein.

In some embodiments, the suppression efficiency of the O-RS and the O-tRNA together is about, e.g., 5 fold, 10 fold, 15 fold, 20 fold, or 25 fold or more greater than the suppression efficiency of the O-tRNA lacking the O-RS. In some aspect, the suppression efficiency of the O-RS and the O-tRNA together is at least about, e.g., 35%, 40%, 45%, 50%, 60%, 75%, 80%, or 90% or more of the suppression efficiency of an orthogonal synthetase pair as set forth in the sequence listings herein.

The host cell uses the O-tRNA/O-RS pair to incorporate the unnatural amino acid into a growing polypeptide chain, e.g., via a nucleic acid that comprises a polynucleotide that encodes a polypeptide of interest, where the polynucleotide comprises a selector codon that is recognized by the O-tRNA. In certain preferred aspects, the cell can include one or more additional O-tRNA/O-RS pairs, where the additional O-tRNA is loaded by the additional O-RS with a different unnatural amino acid. For example, one of the O-tRNAs can recognize a four base codon and the other O-tRNA can recognize a stop codon. Alternately, multiple different stop codons or multiple different four base codons can be used in the same coding nucleic acid.

As noted, in some embodiments, there exists multiple O-tRNA/O-RS pairs in a cell or other translation system, which allows incorporation of more than one unnatural amino acid into a polypeptide. For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an amber selector codon), can further comprise a second orthogonal pair, where the second O-tRNA recognizes a different selector codon, e.g., an opal codon, a four-base codon, or the like. Desirably, the different orthogonal pairs are derived from different sources, which can facilitate recognition of different selector codons.

In certain embodiments, systems comprise a cell such as an *E. coli* cell that includes an orthogonal tRNA (O-tRNA), an orthogonal aminoacyl-tRNA synthetase (O-RS), an unnatural amino acid and a nucleic acid that comprises a polynucleotide that encodes a polypeptide of interest, where the polynucleotide comprises the selector codon that is recognized by the O-tRNA. The translation system can also be a cell-free system, e.g., any of a variety of commercially available "in vitro" transcription/translation systems in combination with an O-tRNA/O-RS pair and an unnatural amino acid as described herein.

The O-tRNA and/or the O-RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases. A second strategy for generating an orthogonal pair involves generating mutant libraries from which to screen and/or select an O-tRNA or O-RS. These strategies can also be combined.

Orthogonal tRNA (O-tRNA)

An orthogonal tRNA (O-tRNA) of the invention desirably mediates incorporation of an unnatural amino acid into a protein that is encoded by a polynucleotide that comprises a selector codon that is recognized by the O-tRNA, e.g., in vivo or in vitro. In certain embodiments, an O-tRNA of the invention includes at least about, e.g., a 45%, a 50%, a 60%, a 75%, a 80%, or a 90% or more suppression efficiency in the presence of a cognate synthetase in response to a selector codon as compared to an O-tRNA comprising or encoded by a polynucleotide sequence as set forth in the O-tRNA sequences in the sequence listing herein.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Examples of O-tRNAs of the invention are set forth in the sequence listing herein, for example, see FIG. 2 and SEQ ID NO: 1. The disclosure herein also provides guidance for the design of additional equivalent O-tRNA species. In an RNA molecule, such as an O-RS mRNA, or O-tRNA molecule, thymine (T) is replace with uracil (U) relative to a given sequence (or vice versa for a coding DNA), or complement thereof. Additional modifications to the bases can also be present to generate largely functionally equivalent molecules.

The invention also encompasses conservative variations of O-tRNAs corresponding to particular O-tRNAs herein. For example, conservative variations of O-tRNA include those molecules that function like the particular O-tRNAs, e.g., as in the sequence listing herein and that maintain the tRNA L-shaped structure by virtue of appropriate self-complementarity, but that do not have a sequence identical to those, e.g., in the sequence listing or FIG. 2, and desirably, are other than wild type tRNA molecules.

The composition comprising an O-tRNA can further include an orthogonal aminoacyl-tRNA synthetase (O-RS), where the O-RS preferentially aminoacylates the O-tRNA with an unnatural amino acid. In certain embodiments, a composition including an O-tRNA can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these can also be present in the cell.

Methods of producing an orthogonal tRNA (O-tRNA) are also a feature of the invention. An O-tRNA produced by the method is also a feature of the invention. In certain embodiments of the invention, the O-tRNAs can be produced by generating a library of mutants. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof, e.g., of the O-tRNA of SEQ ID NO: 1.

Additional mutations can be introduced at a specific position(s), e.g., at a nonconservative position(s), or at a conservative position, at a randomized position(s), or at a combination of both in a desired loop or region of a tRNA, e.g., an anticodon loop, the acceptor stem, D arm or loop, variable loop, TPC arm or loop, other regions of the tRNA molecule, or a combination thereof. Typically, mutations in a tRNA include mutating the anticodon loop of each member of the library of mutant tRNAs to allow recognition of a selector codon. The method can further include adding additional sequences to the O-tRNA. Typically, an O-tRNA possesses an improvement of orthogonality for a desired organism compared to the starting material, e.g., the plurality of tRNA sequences, while preserving its affinity towards a desired RS.

The methods optionally include analyzing the similarity (and/or inferred homology) of sequences of tRNAs and/or aminoacyl-tRNA synthetases to determine potential candidates for an O-tRNA, O-RS and/or pairs thereof, that appear to be orthogonal for a specific organism. Computer programs known in the art and described herein can be used for the analysis, e.g., BLAST and pileup programs can be used. In one example, to choose potential orthogonal translational components for use in *E. coli*, a synthetase and/or a tRNA is chosen that does not display close sequence similarity to eubacterial organisms.

Typically, an O-tRNA is obtained by subjecting to, e.g., negative selection, a population of cells of a first species, where the cells comprise a member of the plurality of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species.

In certain embodiments, in the negative selection, a selector codon(s) is introduced into a polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense (e.g., stop) or frameshift mutations introduced into a polynucleotide that encodes a negative selection marker, e.g., a gene for β-lactamase (bla). For example, polynucleotide variants, e.g., bla variants, with a selector codon at a certain position (e.g., A184), are constructed. Cells, e.g., bacteria, are transformed with these polynucleotides. In the case of an orthogonal tRNA, which cannot be efficiently charged by endogenous *E. coli* synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease or barnase), when a member of the plurality of potential tRNAs is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal tRNAs or non-functional tRNAs survive.

In one embodiment, the pool of tRNAs that are orthogonal to a desired organism are then subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding a cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNA(s), or tRNAs that cannot efficiently be recognized by the synthetase of interest. The cell harboring the non-functional tRNAs or tRNAs that are not efficiently recognized by the synthetase of interest, are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation, survive both selections.

Accordingly, the same marker can be either a positive or negative marker, depending on the context in which it is screened. That is, the marker is a positive marker if it is screened for, but a negative marker if screened against.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In some aspects of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O-RS, and an O-tRNA/O-RS pair that loads an unnatural amino acid in response to a selector codon. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See also, Francisco, J. A., et al., (1993) *Production and fluorescence-activated cell sorting of Escherichia coli expressing a functional antibody fragment on the external surface. Proc Natl Acad Sci USA.* 90:10444-8.

Additional methods for producing a recombinant orthogonal tRNA can be found, e.g., in International Application Publications WO 2002/086075, entitled "METHODS AND COMPOSITIONS FOR THE PRODUCTION OF ORTHOGONAL tRNA AMINOACYL-tRNA SYNTHETASE PAIRS;" WO 2004/094593, entitled "EXPANDING THE EUKARYOTIC GENETIC CODE;" and WO 2005/019415, filed Jul. 7, 2004. See also Forster et al., (2003) *Programming peptidomimetic synthetases by translating genetic codes designed de novo PNAS* 100(11):6353-6357; and, Feng et al., (2003), *Expanding tRNA recognition of a tRNA synthetase by a single amino acid change, PNAS* 100 (10): 5676-5681.

Orthogonal Aminoacyl-tRNA Synthetase (O-RS)

An O-RS of the invention preferentially aminoacylates an O-tRNA with an unnatural amino acid, in vitro or in vivo. An O-RS of the invention can be provided to the translation system, e.g., a cell, by a polypeptide that includes an O-RS and/or by a polynucleotide that encodes an O-RS or a portion thereof. For example, an example O-RS comprises an amino acid sequence as set forth in SEQ ID NO: 4, 6 or 8, or a conservative variation thereof. In another example, an O-RS, or a portion thereof, is encoded by a polynucleotide sequence that encodes an amino acid comprising sequence in the sequence listing or examples herein, or a complementary polynucleotide sequence thereof. See, e.g., the polynucleotide of SEQ ID NO: 5, 7 or 9.

Methods for identifying an orthogonal aminoacyl-tRNA synthetase (O-RS), e.g., an O-RS, for use with an O-tRNA, are also a feature of the invention. For example, a method includes subjecting to selection, e.g., positive selection, a population of cells of a first species, where the cells individually comprise: 1) a member of a plurality of aminoacyl-tRNA synthetases (RSs), (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes an (e.g., positive) selection marker and comprises at least one selector codon. Cells are selected or screened for those that show an enhancement in suppression efficiency compared to cells lacking or with a reduced amount of the member of the plurality of RSs. Suppression efficiency can be measured by techniques known in the art and as described herein. Cells having an enhancement in suppression efficiency comprise an active RS that aminoacylates the O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled unnatural amino acid). The active RS that more efficiently aminoacylates the second set of tRNAs compared to the first set of tRNAs is typically selected, thereby providing an efficient (optimized) orthogonal aminoacyl-tRNA synthetase for use with the O-tRNA. An O-RS, identified by the method, is also a feature of the invention.

Any of a number of assays can be used to determine aminoacylation. These assays can be performed in vitro or in vivo. For example, in vitro aminoacylation assays are described in, e.g., Hoben and Soll (1985) *Methods Enzymol.* 113:55-59. Aminoacylation can also be determined by using a reporter along with orthogonal translation components and detecting the reporter in a cell expressing a polynucleotide comprising at least one selector codon that encodes a protein. See also, WO 2002/085923, entitled "IN VIVO INCORPORATION OF UNNATURAL AMINO ACIDS;" and WO 2004/094593, entitled "EXPANDING THE EUKARYOTIC GENETIC CODE."

Identified O-RS can be further manipulated to alter substrate specificity of the synthetase, so that only a desired unnatural amino acid, but not any of the common 20 amino acids, are charged to the O-tRNA. Methods to generate an orthogonal aminoacyl-tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid. In some aspects of the invention, the steps are performed multiple times, e.g., at least two times.

Additional levels of selection/screening stringency can also be used in the methods of the invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general details for producing O-RS, and altering the substrate specificity of the synthetase can be found in Internal Publication Number WO 2002/086075, entitled "METHODS AND COMPOSITIONS FOR THE PRODUCTION OF ORTHOGONAL tRNA AMINOACYL-tRNA SYNTHETASE PAIRS;" and WO 2004/094593, entitled "EXPANDING THE EUKARYOTIC GENETIC CODE." See also, Wang and Schultz "Expanding the Genetic Code," *Angewandte Chemie Int. Ed.*, 44(1):34-66 (2005), the content of which is incorporated by reference in its entirety.

Source and Host Organisms

The orthogonal translational components (O-tRNA and O-RS) of the invention can be derived from any organism (or a combination of organisms) for use in a host translation system from any other species, with the caveat that the O-tRNA/O-RS components and the host system work in an orthogonal manner. It is not a requirement that the O-tRNA and the O-RS from an orthogonal pair be derived from the same organism. In some aspects, the orthogonal components are derived from Archaea genes (i.e., archaebacteria) for use in a eubacterial host system.

For example, the orthogonal O-tRNA can be derived from an Archae organism, e.g., an archaebacterium, such as *Methanococcus jannaschii, Methanobacterium thermoautotrophi-* cum, Halobacterium such as Haloferax volcanii and Halobacterium species NRC-1, Archaeoglobus fulgidus, Pyrococcus furiosus, Pyrococcus horikoshii, Aeuropyrum pernix, Methanococcus maripaludis, Methanopyrus kandleri, Methanosarcina mazei (Mm), Pyrobaculum aerophilum, Pyrococcus abyssi, Sulfolobus solfataricus (Ss), Sulfolobus tokodaii, Thermoplasma acidophilum, Thermoplasma volcanium, or the like, or a eubacterium, such as Escherichia coli, Thermus thermophilus, Bacillus subtilis, Bacillus stearothermphilus, or the like, while the orthogonal O-RS can be derived from an organism or combination of organisms, e.g., an archaebacterium, such as Methanococcus jannaschii, Methanobacterium thermoautotrophicum, Halobacterium such as Haloferax volcanii and Halobacterium species NRC-1, Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium, or the like, or a eubacterium, such as Escherichia coli, Thermus thermophilus, Bacillus subtilis, Bacillus stearothermphilus, or the like. In one embodiment, eukaryotic sources, e.g., plants, algae, protists, fungi, yeasts, animals (e.g., mammals, insects, arthropods, etc.), or the like, can also be used as sources of O-tRNAs and O-RSs.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms.

The O-tRNA, O-RS or O-tRNA/O-RS pair can be selected or screened in vivo or in vitro and/or used in a cell, e.g., a eubacterial cell, to produce a polypeptide with an unnatural amino acid. The eubacterial cell used is not limited, for example, Escherichia coli, Thermus thermophilus, Bacillus subtilis, Bacillus stearothermphilus, or the like. Compositions of eubacterial cells comprising translational components of the invention are also a feature of the invention.

See also, International Application Publication Number WO 2004/094593, entitled "EXPANDING THE EUKARYOTIC GENETIC CODE," filed Apr. 16, 2004, for screening O-tRNA and/or O-RS in one species for use in another species.

Although orthogonal translation systems (e.g., comprising an O-RS, an O-tRNA and an unnatural amino acid) can utilize cultured host cells to produce proteins having unnatural amino acids, it is not intended that an orthogonal translation system of the invention require an intact, viable host cell. For example, a orthogonal translation system can utilize a cell-free system in the presence of a cell extract. Indeed, the use of cell free, in vitro transcription/translation systems for protein production is a well established technique. Adaptation of these in vitro systems to produce proteins having unnatural amino acids using orthogonal translation system components described herein is well within the scope of the invention.

Selector Codons

Selector codons of the invention expand the genetic codon framework of protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple unnatural amino acids e.g., including at least one unnatural amino acid, using these different selector codons.

In one embodiment, the methods involve the use of a selector codon that is a stop codon for the incorporation of an unnatural amino acid in vivo in a cell. For example, an O-tRNA is produced that recognizes the stop codon and is aminoacylated by an O-RS with an unnatural amino acid. This O-tRNA is not recognized by the naturally occurring host's aminoacyl-tRNA synthetases. Conventional site-directed mutagenesis can be used to introduce the stop codon at the site of interest in a polynucleotide encoding a polypeptide of interest. See, e.g., Sayers, J. R., et al. (1988), 5',3' Exonuclease in phosphorothioate-based oligonucleotide-directed mutagenesis. Nucleic Acids Res, 791-802. When the O-RS, O-tRNA and the nucleic acid that encodes a polypeptide of interest are combined, e.g., in vivo, the unnatural amino acid is incorporated in response to the stop codon to give a polypeptide containing the unnatural amino acid at the specified position. In one embodiment of the invention, the stop codon used as a selector codon is an amber codon, UAG, and/or an opal codon, UGA. In one example, a genetic code in which UAG and UGA are both used as a selector codon can encode 22 amino acids while preserving the ochre nonsense codon, UAA, which is the most abundant termination signal.

The incorporation of unnatural amino acids in vivo can be done without significant perturbation of the host cell. For example in non-eukaryotic cells, such as Escherichia coli, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA. In addition, additional compounds can also be present, e.g., reducing agents such as dithiothretiol (DTT).

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., Biochemistry, 32:7939 (1993). In this case, the synthetic tRNA competes with the naturally occurring tRNA$^{Arg}$, which exists as a minor species in Escherichia coli. In addition, some organisms do not use all triplet codons. An unassigned codon AGA in Micrococcus luteus has been utilized for insertion of amino acids in an in vitro transcription/translation extract. See, e.g., Kowal and Oliver, Nucl. Acid. Res., 25:4685 (1997). Components of the invention can be generated to use these rare codons in vivo.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Methods of the invention include using extended codons based on frameshift suppression. Four or more base codons can insert, e.g., one or multiple unnatural amino acids, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al., (2002) *Exploring the Limits of Codon and Anticodon Size, Chemistry and Biology,* 9:237-244; and, Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.,* 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of tRNA$^{Leu}$ derivatives with NCUA anticodons to suppress UAGN codons (N can be U, A, G, or C), and found that the quadruplet UAGA can be decoded by a tRNA$^{Leu}$ with a UCUA anticodon with an efficiency of 13 to 26% with little decoding in the 0 or −1 frame. See Moore et al., (2000) *J. Mol. Biol.,* 298:195. In one embodiment, extended codons based on rare codons or nonsense codons can be used in invention, which can reduce missense readthrough and frameshift suppression at other unwanted sites. Four base codons have been used as selector codons in a variety of orthogonal systems. See, e.g., WO 2005/019415; WO 2005/007870 and WO 2005/07624. See also, Wang and Schultz "Expanding the Genetic Code," *Angewandte Chemie Int. Ed.,* 44(1):34-66 (2005), the content of which is incorporated by reference in its entirety. While the examples below utilize an amber selector codon, four or more base codons can be used as well, by modifying the examples herein to include four-base O-tRNAs and synthetases modified to include mutations similar to those previously described for various unnatural amino acid O-RSs.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology,* 20:177-182. See also Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool, (2000) *Curr. Opin. Chem. Biol.,* 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool, (2000) *Curr. Opin. Chem. Biol.,* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.,* 121:11586; and Ogawa et al., (2000) *J. Am. Chem. Soc.,* 122:3274. A 3MN:3MN self-pair can be synthesized by KF with efficiency and selectivity sufficient for biological function. See, e.g., Ogawa et al., (2000) *J. Am. Chem. Soc.,* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.,* 123:7439. A novel metallobase pair, Dipic:Py, has also been developed, which forms a stable pair upon binding Cu(II). See Meggers et al., (2000) *J. Am. Chem. Soc.,* 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

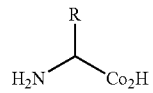

I

An unnatural amino acid is typically any structure having Formula I wherein the R group is any substituent other than one used in the twenty natural amino acids. See e.g., *Biochemistry* by L. Stryer, 3$^{rd}$ ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

Of particular interest herein is the unnatural amino acid phenylselenocysteine (see FIG. 1, structure 1). In addition to the phenylselenocysteine unnatural amino acid, other unnatural amino acids can be simultaneously incorporated into a polypeptide of interest, e.g., using an appropriate second O-RS/O-tRNA pair in conjunction with an orthogonal pair provided by the present invention. Many such additional unnatural amino acids and suitable orthogonal pairs are known. See the present disclosure and the references cited herein. For example, see Wang and Schultz "Expanding the Genetic Code," *Angewandte Chemie Int. Ed.*, 44(1):34-66 (2005); Xie and Schultz, "An Expanding Genetic Code," *Methods* 36(3):227-238 (2005); Xie and Schultz, "Adding Amino Acids to the Genetic Repertoire," *Curr. Opinion in Chemical Biology* 9(6):548-554 (2005); and Wang et al., "Expanding the Genetic Code," *Annu. Rev. Biophys. Biomol. Struct.*, 35:225-249 (2006); the contents of which are each incorporated by reference in their entirety.

Although the phenylselenocysteine unnatural amino acid shown in FIG. 1, structure 1, is of primary interest in the Examples described herein, it is not intended that the invention be strictly limited to that structure. Indeed, a variety of easily-derived, structurally related analogs can be readily produced that retain the principle characteristic of the phenylselenocysteine shown in FIG. 1, structure 1, and also are specifically recognized by the aminoacyl-tRNA synthetases of the invention (e.g., the O-RS of SEQ ID NOS: 4, 6 and 8). It is intended that these related amino acid analogues are within the scope of the invention.

In other unnatural amino acids, for example, R in Formula I optionally comprises an alkyl-, aryl-, acyl-, hydrazine, cyano-, halo-, hydrazide, alkenyl, ether, borate, boronate, phospho, phosphono, phosphine, enone, imine, ester, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, glycosylated amino acids, a saccharide moiety attached to the amino acid side chain, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety.

In another aspect, the invention provides unnatural amino acids having the general structure illustrated by Formula IV below:

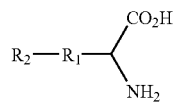

An unnatural amino acid having this structure is typically any structure where $R_1$ is a substituent used in one of the twenty natural amino acids (e.g., tyrosine or phenylalanine) and $R_2$ is a substituent. Thus, this type of unnatural amino acid can be viewed as a natural amino acid derivative.

In addition to unnatural amino acids that contain the phenylselenocysteine structure shown in FIG. 1, structure 1, unnatural amino acids can also optionally comprise modified backbone structures, e.g., as illustrated by the structures of Formula II and III:

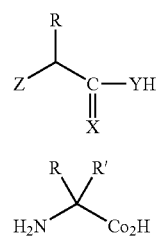

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

In some aspects, the invention utilizes unnatural amino acids in the L-configuration. However, it is not intended that the invention be limited to the use of L-configuration unnatural amino acids. It is contemplated that the D-enantiomers of these unnatural amino acids also find use with the invention.

The unnatural amino acids finding use with the invention is not strictly limited to the phenylselenocysteine unnatural amino acid shown in FIG. 1, structure 1. One of skill in the art will recognize that a wide variety of unnatural analogs of naturally occurring amino acids are easily derived. For example, but not limited to, unnatural derived from tyrosine are readily produced. Tyrosine analogs include, e.g., para-substituted tyrosines, ortho-substituted tyrosines, and meta substituted tyrosines, wherein the substituted tyrosine comprises an alkynyl group, acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenyalanines, and meta-substituted phenylalanines, wherein the substituent comprises an alkynyl group, a hydroxy group, a methoxy group, a methyl group, an allyl group, an aldehyde, a nitro, a thiol group, or keto group, or the like. Specific examples of unnatural amino acids include, but are not limited to, phenylselenocysteine, sulfotyrosine, p-ethylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine and p-nitro-L-phenylalanine. Also, a p-propargyloxyphenylalanine, a 3,4-dihydroxy-L-phenyalanine (DHP), a 3,4,6-trihydroxy-L-phenylalanine, a 3,4,5-trihydroxy-L-phenylalanine, 4-nitro-phenylalanine, a p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a 3-nitro-tyrosine, a 3-thiol-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids are disclosed in the references cited herein. See also, Published International Applications WO 2004/094593, entitled "EXPANDING THE EUKARYOTIC GENETIC CODE;" and WO 2006/110182, entitled "ORTHOGONAL TRANSLATION COMPONENTS FOR THE IN VIVO INCORPORATION OF UNNATURAL AMINO ACIDS," filed Oct. 27, 2005.

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King and Kidd (1949) *A New Synthesis of Glutamine and of γ-Dipeptides of Glutamic Acid from Phthylated Intermediates*. *J. Chem. Soc.*, 3315-3319; Friedman and Chatterrji (1959) *Synthesis of Derivatives of Glutamine as Model Substrates for Anti-Tumor Agents*. *J. Am. Chem. Soc.* 81, 3750-3752; Craig et al. (1988) *Absolute Configuration of the Enantiomers of 7-Chloro-4[[4-(diethylamino)-1-methylbutyl]amino]quinoline (Chloroquine)*. *J. Org. Chem.* 53, 1167-1170; Azoulay et al. (1991) *Glutamine analogues as Potential Antimalarials*, *Eur. J. Med. Chem.* 26, 201-5; Koskinen, and Rapoport (1989) *Synthesis of 4-Substituted Prolines as Conformationally Constrained Amino Acid Analogues*. *J. Org. Chem.* 54, 1859-1866; Christie and Rapoport (1985) *Synthesis of Optically Pure Pipecolates from L-Asparagine. Application to the Total Synthesis of (+)-Apovincamine through Amino Acid Decarbonylation and Iminium Ion Cyclization*. *J. Org. Chem.* 1989:1859-1866; Barton et al., (1987) *Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives*. *Tetrahedron Lett.* 43:4297-4308; and, Subasinghe et al., (1992) *Quisqualic acid analogues: synthesis of beta-heterocyclic 2-aminopropanoic acid derivatives and their activity at a novel quisqualate-sensitized site*. *J. Med. Chem.* 35:4602-7. See also, International Publication WO 2004/058946, entitled "PROTEIN ARRAYS," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., the toxicity assays in, e.g., International Publication WO 2004/058946, entitled "PROTEIN ARRAYS," filed on Dec. 22, 2003; and Liu and Schultz (1999) *Progress toward the evolution of an organism with an expanded genetic code*. PNAS 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.*, 91:10747-10751. A related approach shuffles families of related (e.g., homologous) genes to quickly evolve enzymes with desired characteristics. An example of such "family gene shuffling" methods is found in Crameri et al. (1998) "DNA shuffling of a family of genes from diverse species accelerates directed evolution" *Nature*, 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al. (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See, also, Ostermeier et al. (1999) "Combinatorial Protein Engineering by Incremental Truncation," *Proc. Natl. Acad. Sci. USA*, 96: 3562-67, and Ostermeier et al. (1999), "Incremental Truncation as a Strategy in the Engineering of Novel Biocatalysts," *Biological and Medicinal Chemistry*, 7: 2139-44. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave and Youvan (1993) *Biotechnology Research* 11: 1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" *Biotechnology* 10:297-300; or Reidhaar-Olson et al. (1991) "Random mutagenesis of protein sequences using oligonucleotide cassettes" *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "NON-STOCHASTIC GENERATION OF GENETIC VACCINES AND ENZYMES" WO 00/46344.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of lactobacillus for improved acid tolerance" *Nature Biotechnology* 20(7):707-712; and Zhang et al. (2002) "Genome Shuffling Leads to Rapid Phenotypic Improvement in Bacteria" *Nature* 415(6872):644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" *Curr. Opin. Biotechnol.* 14(5):454-9; Berry et al. (2002) "Application of Metabolic Engineering to improve both the production and use of Biotech Indigo" *J. Industrial Microbiology and Biotechnology* 28:127-133; Banta et al. (2002) "Optimizing an artificial metabolic pathway: Engineering the cofactor specificity of Corynebacterium 2,5-diketo-D-gluconic acid reductase for use in vitamin C biosynthesis" *Biochemistry*, 41(20), 6226-36; Selivonova et al. (2001) "Rapid Evolution of Novel Traits in Microorganisms" *Applied and Environmental Microbiology*, 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Orthogonal Components for Incorporating Unnatural Amino Acids

The invention provides compositions and methods for producing orthogonal components for incorporating the unnatural amino acid phenylselenocysteine (see FIG. 1, structure 1) into a growing polypeptide chain in response to a selector codon, e.g., an amber stop codon, a nonsense codon, a four or more base codon, etc., e.g., in vivo. For example, the invention provides orthogonal-tRNAs (O-tRNAs), orthogonal aminoacyl-tRNA synthetases (O-RSs) and pairs thereof. These pairs can be used to incorporate an unnatural amino acid into growing polypeptide chains.

A composition of the invention includes an orthogonal aminoacyl-tRNA synthetase (O-RS), where the O-RS preferentially aminoacylates an O-tRNA with phenylselenocysteine. In certain embodiments, the O-RS comprises an amino acid sequence comprising SEQ ID NO: 4, 6 or 8, and conservative variations thereof. In certain embodiments of the invention, the O-RS preferentially aminoacylates the O-tRNA over any endogenous tRNA with an the particular unnatural amino acid, where the O-RS has a bias for the O-tRNA, and where the ratio of O-tRNA charged with an unnatural amino acid to the endogenous tRNA charged with the same unnatural amino acid is greater than 1:1, and more preferably where the O-RS charges the O-tRNA exclusively or nearly exclusively.

A composition that includes an O-RS can optionally further include an orthogonal tRNA (O-tRNA), where the O-tRNA recognizes a selector codon. Typically, an O-tRNA of the invention includes at least about, e.g., a 45%, a 50%, a 60%, a 75%, an 80%, or a 90% or more suppression efficiency in the presence of a cognate synthetase in response to a selector codon as compared to the suppression efficiency of an O-tRNA comprising or encoded by a polynucleotide sequence as set forth in the sequence listings (e.g., SEQ ID NO: 1) and examples herein. In one embodiment, the suppression efficiency of the O-RS and the O-tRNA together is, e.g., 5 fold, 10 fold, 15 fold, 20 fold, 25 fold or more greater than the suppression efficiency of the O-tRNA in the absence of an O-RS. In some aspects, the suppression efficiency of the O-RS and the O-tRNA together is at least 45% of the suppression efficiency of an orthogonal tyrosyl-tRNA synthetase pair derived from *Methanococcus jannaschii*.

A composition that includes an O-tRNA can optionally include a cell (e.g., a eubacterial cell, such as an *E. coli* cell and the like, or a eukaryotic cell such as a yeast cell), and/or a translation system.

A cell (e.g., a eubacterial cell or a yeast cell) comprising a translation system is also provided by the invention, where the translation system includes an orthogonal-tRNA (O-tRNA); an orthogonal aminoacyl-tRNA synthetase (O-RS); and, a phenylselenocysteine unnatural amino acid. Typically, the O-RS preferentially aminoacylates the O-tRNA over any endogenous tRNA with the unnatural amino acid, where the O-RS has a bias for the O-tRNA, and where the ratio of O-tRNA charged with the unnatural amino acid to the endogenous tRNA charged with the unnatural amino acid is greater than 1:1, and more preferably where the O-RS charges the O-tRNA exclusively or nearly exclusively. The O-tRNA recognizes the first selector codon, and the O-RS preferentially aminoacylates the O-tRNA with an unnatural amino acid. In one embodiment, the O-tRNA comprises or is encoded by a polynucleotide sequence as set forth in SEQ ID NO: 1, or a complementary polynucleotide sequence thereof. In one embodiment, the O-RS comprises an amino acid sequence as set forth in SEQ ID NO: 4, 6, 8 or 10, and conservative variations thereof.

A cell of the invention can optionally further comprise an additional different O-tRNA/O-RS pair and a second unnatural amino acid, e.g., where this O-tRNA recognizes a second selector codon and this O-RS preferentially aminoacylates the corresponding O-tRNA with the second unnatural amino acid, where the second amino acid is different from the first unnatural amino acid. Optionally, a cell of the invention includes a nucleic acid that comprises a polynucleotide that encodes a polypeptide of interest, where the polynucleotide comprises a selector codon that is recognized by the O-tRNA.

In certain embodiments, a cell of the invention is a eubacterial cell (such as *E. coli*), that includes an orthogonal-tRNA (O-tRNA), an orthogonal aminoacyl-tRNA synthetase (O-RS), an unnatural amino acid, and a nucleic acid that comprises a polynucleotide that encodes a polypeptide of interest, where the polynucleotide comprises the selector codon that is recognized by the O-tRNA. In certain embodiments of the invention, the O-RS preferentially aminoacylates the O-tRNA with the unnatural amino acid with an efficiency that is greater than the efficiency with which the O-RS aminoacylates any endogenous tRNA.

In certain embodiments of the invention, an O-tRNA of the invention comprises or is encoded by a polynucleotide sequence as set forth in the sequence listings (e.g., SEQ ID NO: 1) or examples herein, or a complementary polynucleotide sequence thereof. In certain embodiments of the invention, an O-RS comprises an amino acid sequence as set forth in the sequence listings, or a conservative variation thereof. In one embodiment, the O-RS or a portion thereof is encoded by a polynucleotide sequence encoding an amino acid as set forth in the sequence listings or examples herein, or a complementary polynucleotide sequence thereof.

The O-tRNA and/or the O-RS of the invention can be derived from any of a variety of organisms (e.g., eukaryotic and/or non-eukaryotic organisms).

Polynucleotides are also a feature of the invention. A polynucleotide of the invention (e.g., SEQ ID NO: 5, 7 or 9) includes an artificial (e.g., man-made, and not naturally occurring) polynucleotide comprising a nucleotide sequence encoding a polypeptide as set forth in the sequence listings herein, and/or is complementary to or that polynucleotide sequence. A polynucleotide of the invention can also include a nucleic acid that hybridizes to a polynucleotide described above, under highly stringent conditions, over substantially the entire length of the nucleic acid. A polynucleotide of the invention also includes a polynucleotide that is, e.g., at least 75%, at least 80%, at least 90%, at least 95%, at least 98% or more identical to that of a naturally occurring tRNA or corresponding coding nucleic acid (but a polynucleotide of the invention is other than a naturally occurring tRNA or corresponding coding nucleic acid), where the tRNA recognizes a selector codon, e.g., a four base codon. Artificial polynucleotides that are, e.g., at least 80%, at least 90%, at least 95%, at least 98% or more identical to any of the above and/or a polynucleotide comprising a conservative variation of any the above, are also included in polynucleotides of the invention.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods of producing components of an O-tRNA/O-RS pair are also features of the invention. Components produced by these methods are also a feature of the invention. For example, methods of producing at least one tRNA that is orthogonal to a cell (O-tRNA) include generating a library of mutant tRNAs; mutating an anticodon loop of each member of the library of mutant tRNAs to allow recognition of a selector codon, thereby providing a library of potential O-tRNAs, and subjecting to negative selection a first population of cells of a first species, where the cells comprise a member of the library of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species, thereby providing at least one O-tRNA. An O-tRNA produced by the methods of the invention is also provided.

In certain embodiments, the methods further comprise subjecting to positive selection a second population of cells of the first species, where the cells comprise a member of the pool of tRNAs that are orthogonal to the cell of the first species, a cognate aminoacyl-tRNA synthetase, and a positive selection marker. Using the positive selection, cells are selected or screened for those cells that comprise a member of the pool of tRNAs that is aminoacylated by the cognate aminoacyl-tRNA synthetase and that shows a desired response in the presence of the positive selection marker, thereby providing an O-tRNA. In certain embodiments, the second population of cells comprise cells that were not eliminated by the negative selection.

Methods for identifying an orthogonal-aminoacyl-tRNA synthetase that charges an O-tRNA with an unnatural amino acid are also provided. For example, methods include subjecting a population of cells of a first species to a selection, where the cells each comprise: 1) a member of a plurality of aminoacyl-tRNA synthetases (RSs), (e.g., the plurality of RSs can include mutant RSs, RSs derived from a species other than a first species or both mutant RSs and RSs derived from a species other than a first species); 2) the orthogonal-tRNA (O-tRNA) (e.g., from one or more species); and 3) a polynucleotide that encodes a positive selection marker and comprises at least one selector codon.

Cells (e.g., a host cell) are selected or screened for those that show an enhancement in suppression efficiency compared to cells lacking or having a reduced amount of the member of the plurality of RSs. These selected/screened cells comprise an active RS that aminoacylates the O-tRNA. An orthogonal aminoacyl-tRNA synthetase identified by the method is also a feature of the invention.

Methods of producing a protein in a cell (e.g., in a eubacterial cell such as an *E. coli* cell or the like, or in a yeast cell) having the unnatural amino acid at a selected position are also a feature of the invention. For example, a method includes growing, in an appropriate medium, a cell, where the cell comprises a nucleic acid that comprises at least one selector codon and encodes a protein, providing the unnatural amino acid, and incorporating the unnatural amino acid into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the unnatural amino acid. A protein produced by this method is also a feature of the invention.

The invention also provides compositions that include proteins, where the proteins comprise phenylselenocysteine. In certain embodiments, the protein comprises an amino acid sequence that is at least 75% identical to that of a known protein, e.g., human growth hormone, a therapeutic protein, a diagnostic protein, an industrial enzyme, or portion thereof. Optionally, the composition comprises a pharmaceutically acceptable carrier.

Nucleic Acid and Polypeptide Sequences and Variants

As described herein, the invention provides polynucleotide sequences encoding, e.g., O-tRNAs and O-RSs, and polypeptide amino acid sequences, e.g., O-RSs, and, e.g., compositions, systems and methods comprising said polynucleotide or polypeptide sequences. Examples of said sequences, e.g., O-tRNA and O-RS amino acid and nucleotide sequences are disclosed herein (see FIG. 2). However, one of skill in the art will appreciate that the invention is not limited to those sequences specifically recited herein, e.g., in the Examples and sequence listing. One of skill will appreciate that the invention also provides many related sequences with the functions described herein, e.g., polynucleotides and polypeptides encoding conservative variants of an O-RS disclosed herein.

The construction and analysis of orthogonal synthetase species (O-RS) that are able to aminoacylate a cognate O-tRNA with phenylselenocysteine are described in Example 1. This Example describes the construction and analysis of the O-RS species that are able to incorporate the unnatural amino acid phenylselenocysteine.

The invention provides polypeptides (O-RSs) and polynucleotides, e.g., O-tRNA, polynucleotides that encode O-RSs or portions thereof, oligonucleotides used to isolate aminoacyl-tRNA synthetase clones, etc. Polynucleotides of the invention include those that encode proteins or polypeptides of interest of the invention with one or more selector codon. In addition, polynucleotides of the invention include, e.g., a polynucleotide comprising a nucleotide sequence as set forth in SEQ ID NO: 5, 7 or 9, and a polynucleotide that is complementary to or that encodes a polynucleotide sequence thereof. A polynucleotide of the invention also includes any polynucleotide that encodes an O-RS amino acid sequence comprising SEQ ID NO: 4, 6 or 8. Similarly, an artificial nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention. An artificial polynucleotide is a polynucleotide that is man made and is not naturally occurring.

A polynucleotide of the invention also includes an artificial polynucleotide that is, e.g., at least 75%, at least 80%, at least 90%, at least 95%, at least 98% or more identical to that of a naturally occurring tRNA, (but is other than a naturally occurring tRNA). A polynucleotide also includes an artificial polynucleotide that is, e.g., at least 75%, at least 80%, at least 90%, at least 95%, at least 98% or more identical (but not 100% identical) to that of a naturally occurring tRNA.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

| Conservative Amino Acid Substitutions | | | | |
|---|---|---|---|---|
| Nonpolar and/or Aliphatic Side Chains | Polar, Uncharged Side Chains | Aromatic Side Chains | Positively Charged Side Chains | Negatively Charged Side Chains |
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, including conservative variations of nucleic acids of the invention, and this comparative hybridization method is a preferred method of distinguishing nucleic acids of the invention. In addition, target nucleic acids which hybridize to a nucleic acid represented by SEQ ID NO: 5, 7, 9 or 11, under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes*, Part I, Chapter 2, "Overview of Principles of Hybridization and the Strategy of Nucleic Acid Probe Assays," (Elsevier, New York), as well as in *Current Protocols In Molecular Biology*, Ausubel et al., eds., *Current Protocols*, a joint venture between Greene Publishing Associates, Inc. and John Wiley & Sons, Inc., (supplemented through 2004); and Hames and Higgins (1995), *Gene Probes* 1 *and Gene Probes* 2, both from IRL Press at Oxford University Press, Oxford, England, provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook et al. for a description of SSC buffer; Sambrook et al., *Molecular Cloning—A Laboratory Manual* (3rd Ed.), Vol. 1-3, Cold Spring Harbor Laboratory, Cold Spring Harbor, N.Y., 2001). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes*, Part I, Chapter 2, "Overview of Principles of Hybridization and the Strategy of Nucleic Acid Probe Assays," (Elsevier, New York); and in Hames and Higgins (1995), *Gene Probes* 1 *and Gene Probes* 2, both from IRL Press at Oxford University Press, Oxford, England. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In some aspects, the invention provides a nucleic acid that comprises a unique subsequence in a nucleic acid selected from the sequences of O-tRNAs and O-RSs disclosed herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the invention or related nucleic acids.

Similarly, the invention includes a polypeptide which comprises a unique subsequence in a polypeptide selected from the sequences of O-RSs disclosed herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols In Molecular Biology*, Ausubel et al., eds., *Current Protocols*, a joint venture between Greene Publishing Associates, Inc. and John Wiley & Sons, Inc., (supplemented through 2004).

One example of an algorithm that is suitable for determining percent sequence identity and sequence similarity is the BLAST algorithm, which is described in Altschul et al., *J. Mol. Biol.*, 215:403-410 (1990). Software for performing BLAST analyses is publicly available through the National Center for Biotechnology Information (see the NCBI website). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., (1990) *J. Mol. Biol.*, 215:403-410). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotide and polypeptides of the invention and used in the invention can be manipulated using molecular biological techniques. General texts which describe molecular biological techniques include Berger and Kimmel, *Guide to Molecular Cloning Techniques, Methods in Enzymology*, volume 152 (1987), Academic Press, Inc., San Diego, Calif.; Sambrook et al., *Molecular Cloning—A Laboratory Manual* (3rd Ed.), Vol. 1-3, Cold Spring Harbor Laboratory, Cold Spring Harbor, N.Y., 2001 and *Current Protocols In Molecular Biology*, Ausubel et al., eds., *Current Protocols*, a joint venture between Greene Publishing Associates, Inc. and John Wiley & Sons, Inc., (supplemented through 2004)). These texts describe mutagenesis, the use of vectors, promoters and many other relevant topics related to, e.g., the generation of genes that include selector codons for production of proteins that include unnatural amino acids, orthogonal tRNAs, orthogonal synthetases, and pairs thereof.

Various types of mutagenesis are used in the invention, e.g., to mutate tRNA molecules, to produce libraries of tRNAs, to produce libraries of synthetases, to insert selector codons that encode an unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman and Smith, *Gene* 8:81 (1979); Roberts et al., *Nature*, 328:731 (1987); Schneider et al., *Protein Expr. Purif.* 6435:10 (1995); *Current Protocols In Molecular Biology*, Ausubel et al., Eds., *Current Protocols*, a joint venture between Greene Publishing Associates, Inc. and John Wiley & Sons, Inc., (supplemented through 2004); Sambrook et al., *Molecular Cloning—A Laboratory Manual* (3rd Ed.), Vol. 1-3, Cold Spring Harbor Laboratory, Cold Spring Harbor, New York, 2001; and Berger and Kimmel, *Guide to Molecular Cloning Techniques, Methods in Enzymology*, volume 152 (1987), Academic Press, Inc., San Diego, Calif. The vector can be, for example, in the form of a plasmid, a bacterium, a virus, a naked polynucleotide, or a conjugated polynucleotide. The vectors are introduced into cells and/or microorganisms by standard methods including electroporation (Fromm et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)), and/or the like.

A highly efficient and versatile single plasmid system was developed for site-specific incorporation of unnatural amino acids into proteins in response to the amber stop codon (UAG) in *E. coli*. In the new system, the pair of *M. jannaschii* suppressor tRNAtyr(CUA) and tyrosyl-tRNA synthetase are encoded in a single plasmid, which is compatible with most *E. coli* expression vectors. Monocistronic tRNA operon under control of proK promoter and terminator was constructed for optimal secondary structure and tRNA processing. Introduction of a mutated form of glnS promoter for the synthetase resulted in a significant increase in both suppression efficiency and fidelity. Increases in suppression efficiency were also obtained by multiple copies of tRNA gene as well as by a specific mutation (D286R) on the synthetase (Kobayashi et al., "Structural basis for orthogonal tRNA specificities of tyrosyl-tRNA synthetases for genetic code expansion," Nat. Struct. Biol., 10(6):425-432 [2003]). The generality of the optimized system was also demonstrated by highly efficient and accurate incorporation of several different unnatural amino acids, whose unique utilities in studying protein function and structure were previously proven.

A catalogue of Bacteria and Bacteriophages useful for cloning is provided, e.g., by the ATCC, e.g., *The ATCC Catalogue of Bacteria and Bacteriophage* (1996) Gherna et al. (eds) published by the ATCC. Additional basic procedures for sequencing, cloning and other aspects of molecular biology and underlying theoretical considerations are also found in Sambrook et al., *Molecular Cloning—A Laboratory Manual* (3rd Ed.), Vol. 1-3, Cold Spring Harbor Laboratory, Cold Spring Harbor, N.Y., 2001; *Current Protocols In Molecular Biology*, Ausubel et al., eds., *Current Protocols*, a joint venture between Greene Publishing Associates, Inc. and John Wiley & Sons, Inc., (supplemented through 2004); and in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex.), The Great American Gene Company (Ramona, Calif.), Express-Gen Inc. (Chicago, Ill.), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Proteins and Polypeptides of Interest

Methods of producing a protein in a cell with an unnatural amino acid at a specified position are also a feature of the invention. For example, a method includes growing, in an appropriate medium, the cell, where the cell comprises a nucleic acid that comprises at least one selector codon and encodes a protein; and, providing the unnatural amino acid; where the cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the unnatural amino acid. A protein produced by this method is also a feature of the invention.

In certain embodiments, the O-RS comprises a bias for the aminoacylation of the cognate O-tRNA over any endogenous tRNA in an expression system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The invention also provides compositions that include proteins, where the proteins comprise an unnatural amino acid. In certain embodiments, the protein comprises an amino acid sequence that is at least 75% identical to that of a therapeutic protein, a diagnostic protein, an industrial enzyme, or portion thereof.

The compositions of the invention and compositions made by the methods of the invention optionally are in a cell. The O-tRNA/O-RS pairs or individual components of the invention can then be used in a host system's translation machinery, which results in an unnatural amino acid being incorporated into a protein. International Publication Numbers WO 2004/094593, filed Apr. 16, 2004, entitled "EXPANDING THE EUKARYOTIC GENETIC CODE," and WO 2002/085923, entitled "IN VIVO INCORPORATION OF UNNATURAL AMINO ACIDS," describe this process, and are incorporated herein by reference. For example, when an O-tRNA/O-RS pair is introduced into a host, e.g., an *Escherichia coli* cell, the pair leads to the in vivo incorporation of an unnatural amino acid such as phenylselenocysteine into a protein in response to a selector codon. The unnatural amino acid that is added to the system can be a synthetic amino acid, such as a derivative of a phenylalanine or tyrosine, which can be exogenously added to the growth medium. Optionally, the compositions of the present invention can be in an in vitro translation system, or in an in vivo system(s).

A cell of the invention provides the ability to synthesize proteins that comprise unnatural amino acids in large useful quantities. In some aspects, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the protein that comprises an unnatural amino acid, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 nL to about 100 L). The production of large quantities (e.g., greater that that typically possible with other methods, e.g., in vitro translation) of a protein in a cell including at least one unnatural amino acid is a feature of the invention.

The incorporation of an unnatural amino acid can be done to, e.g., tailor changes in protein structure and/or function, e.g., to change size, acidity, nucleophilicity, hydrogen bonding, hydrophobicity, accessibility of protease target sites, target to a moiety (e.g., for a protein array), incorporation of labels or reactive groups, etc. Proteins that include an unnatural amino acid can have enhanced or even entirely new catalytic or physical properties. For example, the following properties are optionally modified by inclusion of an unnatural amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one unnatural amino acid are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology,* 4:645-652.

In some aspects of the invention, a composition includes at least one protein with at least one, e.g., at least two, at least three, at least four, at least five, at least six, at least seven, at least eight, at least nine, or at least ten or more unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is an unnatural amino acid. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any protein (or portion thereof) that includes an unnatural amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more unnatural amino acid can be found, but not limited to, those in International Publications WO 2004/094593, filed Apr. 16, 2004, entitled "EXPANDING THE EUKARYOTIC GENETIC CODE;" and, WO 2002/085923, entitled "IN VIVO INCORPORATION OF UNNATURAL AMINO ACIDS." Examples of therapeutic, diagnostic, and other proteins that can be modified to comprise one or more unnatural amino acids include, but are not limited to, e.g., hirudin, human growth hormone, RAS, Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C-X-C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), superoxide dismutase (SOD), toxic shock syndrome toxin (TSST-1), thymosin alpha 1, Tissue plasminogen activator, tumor necrosis factor beta (TNF beta), tumor necrosis factor receptor (TNFR), tumor necrosis factor-alpha (TNF alpha), vascular Endothelial Growth Factor (VEGEF), urokinase and many others.

One class of proteins that can be made using the compositions and methods for in vivo incorporation of unnatural amino acids described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more unnatural amino acids) include biologically active proteins such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one unnatural amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases; nitrile hydratases, nitrilases, proteases, phosphatases, subtilisins, transaminase, and nucleases.

Many of these proteins are commercially available (See, e.g., Sigma BioSciences), and the corresponding protein sequences and genes, and typically, many variants thereof, are well-known (see, e.g., Genbank). Any of them can be modified by the insertion of one or more unnatural amino acid according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, enzymatic activity, production capability, or the like.

A variety of other proteins can also be modified to include one or more unnatural amino acid using compositions and methods of the invention. For example, the invention can include substituting one or more natural amino acids in one or more vaccine proteins with an unnatural amino acid, e.g., in proteins from infectious fungi, e.g., *Aspergillus, Candida* species; bacteria, particularly *E. coli*, which serves a model for pathogenic bacteria, as well as medically important bacteria such as *Staphylococci* (e.g., *aureus*), or *Streptococci* (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for unnatural amino acid modification.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of an unnatural amino acid. For example, a nucleic acid for a protein of interest is mutagenized to include one or more selector codon, providing for the insertion of the one or more unnatural amino acids. The invention includes any such variant, e.g., mutant, versions of any protein, e.g., including at least one unnatural amino acid. Similarly, the invention also includes corresponding nucleic acids, i.e., any nucleic acid with one or more selector codon that encodes one or more unnatural amino acid.

To make a protein that includes an unnatural amino acid, one can use host cells and organisms that are adapted for the in vivo incorporation of the unnatural amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., polypeptides comprising unnatural amino acids in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional details on proteins, antibodies, antisera, etc. can be found in International Publication Numbers WO 2004/094593, entitled "EXPANDING THE EUKARYOTIC GENETIC CODE;" WO 2002/085923, entitled "IN VIVO INCORPORATION OF UNNATURAL AMINO ACIDS;" WO 2004/035605, entitled "GLYCOPROTEIN SYNTHESIS;" and WO 2004/058946, entitled "PROTEIN ARRAYS."

Use of O-tRNA and O-RS and O-tRNA/O-RS Pairs

The compositions of the invention and compositions made by the methods of the invention optionally are in a cell. The O-tRNA/O-RS pairs or individual components of the invention can then be used in a host system's translation machinery, which results in an unnatural amino acid being incorporated into a protein. International Publication Number WO 2002/085923 by Schultz, et al., entitled "IN VIVO INCORPORATION OF UNNATURAL AMINO ACIDS," describes this process and is incorporated herein by reference. For example, when an O-tRNA/O-RS pair is introduced into a host, e.g., Escherichia coli or yeast, the pair leads to the in vivo incorporation of an unnatural amino acid, which can be exogenously added to the growth medium, into a protein, e.g., a myoglobin test protein or a therapeutic protein, in response to a selector codon, e.g., an amber nonsense codon. Optionally, the compositions of the invention can be in an in vitro translation system, or in a cellular in vivo system(s). Proteins with the unnatural amino acid can be used in any of a wide range of applications. For example, the unnatural moiety incorporated into a protein can serve as a target for any of a wide range of modifications, for example, crosslinking with other proteins, with small molecules such as labels or dyes and/or biomolecules. With these modifications, incorporation of the unnatural amino acid can result in improved therapeutic proteins and can be used to alter or improve the catalytic function of enzymes. In some aspects, the incorporation and subsequent modification of an unnatural amino acid in a protein can facilitate studies on protein structure, interactions with other proteins, and the like.

Kits

Kits are also a feature of the invention. For example, a kit for producing a protein that comprises at least one unnatural amino acid in a cell is provided, where the kit includes at least one container containing a polynucleotide sequence encoding an O-tRNA, and/or an O-tRNA, and/or a polynucleotide sequence encoding an O-RS, and/or an O-RS. In one embodiment, the kit further includes the unnatural amino acid phenylselenocysteine. In another embodiments, the kit further comprises instructional materials for producing the protein and/or a host cell.

EXAMPLES

The following examples are offered to illustrate, but not to limit the claimed invention. One of skill will recognize a variety of non-critical parameters that may be altered without departing from the scope of the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example

Genetic Selection of Mutant Synthetases Specific for Phenylselenocysteine

Phenylselenocysteine Reactive Chemistry

Selenium is an essential element in both organic synthesis and biology. It has been demonstrated that a phenylseleno moiety can be oxidized in mild conditions, and spontaneous syn elimination of the selenoxide results in olefin formation. This strategy has been used extensively in total synthesis.

The incorporation of an unnatural amino acid containing selenium into proteins would create an attractive target for highly selective posttranslational modification of proteins, for example, to produce selectively lipidated proteins. One such unnatural seleno amino acid is phenylselenocysteine (CAS Registry Number 71128-82-0), synonymously termed phenylselenide or Se-Phenyl-L-selenocysteine. This structure is provided in FIG. 1, structure 1. This unnatural amino acid can be obtained, for example, from Sigma®-Aldrich® Co., Inc., catalog number 50827.

Oxidative cleavage of a phenylselenocysteine amino acid residue results in the $\alpha,\beta$-unsaturated amino acid dehydroalanine (see FIG. 1, structure 2). Dehydroalanine is found in a number of naturally occurring peptides (Chatterjee et al. (2005), *Chemical Reviews* 105(2):633-683). Dehydropeptides containing unprotected cysteine residues undergo intramolecular stereoselective conjugate addition to produce cyclic lanthionines (Chatterjee et al. (2005), *Chemical Reviews* 105(2):633-683). Lanthionines are structures that are found in lantibiotics, a class of post-translationally modified antibiotics (Chatterjee et al. (2005), *Chemical Reviews* 105(2):633-683).

Michael Addition reactions of the unnatural amino acid dehydroalanine (see FIG. 1, structure 2) can result in proteins with post-translational modifications, for example, by reaction with a thio-lipid to generate a lipidated protein. More specifically, reaction with thiopalmitic acid results in palmitoylcysteine (see FIG. 1, structure 3), reaction with farnesylmercaptan affords farnesylcysteine (see FIG. 1, structure 4), and reaction with malonate produces γ-carboxyglutamic acid (see FIG. 1, structure 6). In addition, reaction with 1-hexadecanethiol results in S-hexadecylcysteine (see FIG. 1, structure 5). Although S-hexadecylcysteine is not a native post-translational modification, the presence of this residue in protein can have desired properties; for example, it can result in human serum albumin binding, and higher protein stability in vivo.

The lipidation of polypeptides by targeted modification of phenylselenocysteine residues can have desired properties, such as membrane localization, improved in vivo stability (i.e., improved half-life) and lipid solubility. Furthermore, the lipidated forms of some proteins are the biologically active forms.

Production of Proteins Comprising Phenylselenocysteine

Methodologies that allow the systematic addition of unnatural amino acids to the genetic codes of *E. coli*, yeast and mammalian cells have been previously described. Such methods are based on the evolution of a nonsense suppressor tRNA and an aminoacyl-tRNA synthetase (RS) pair that has the property of orthogonality, defined as the ability to selectively incorporate a given amino acid in response to a unique codon without cross-reacting with endogenous host tRNAs, aminoacyl-tRNA synthetases, or amino acids.

The present invention provides compositions and methods for the in vivo generation of polypeptides containing the unnatural amino acid phenylselenocysteine by creation of orthogonal reagents that permit the genetically programmed translational incorporation of this unnatural amino acid directly into a growing polypeptide chain. Furthermore, the use of these orthogonal systems allows the production of large quantities of polypeptides containing the unnatural amino acid (i.e., much larger quantities of the polypeptides than would be possible using other synthesis methods). Polypeptides comprising phenylselenocysteine can be used in targeted modification reactions, for example but not limited to, the generation of artificially lipidated polypeptides according to the teachings of the present specification. Such modified proteins find a variety of uses, including but not limited to improved therapeutic agents.

To generate an orthogonal tRNA/aaRS pair that uniquely inserts phenylselenocysteine (FIG. 1., structure 1), a library of active site mutants of the *Methanococcus jannaschii* tyrosyl-tRNA synthetase (MjTyrRS), which specifically charges an engineered *M. jannaschii* nonsense suppressor (MjtRNA$^{Tyr}_{CUA}$) not recognized by *E. coli* synthetases, was used. The synthetase library pBK-lib5, as described in Wang et al. (2006), *Annual Review of Biophysics and Biomolecular Structure* 35:225-249, was used in the screening and subjected to a series of positive and negative selections. Survival in the positive selection was contingent upon suppression of an amber mutation in the chloramphenicol acetyltransferase (CAT) gene in the presence of phenylselenocysteine; survival in the negative selection was contingent upon inadequate suppression of amber mutations in a gene encoding the toxic barnase protein in the absence of phenylselenocysteine. Clones survive through both positive and negative rounds of selection only if they uniquely incorporate phenylselenocysteine in response to the amber codon.

Following these selections, clone candidates were identified that allowed cells harboring the CAT gene with an amber mutation selector codon at a permissive site to survive in the presence of chloramphenicol only in the presence of phenylselenocysteine. In the absence of phenylselenocysteine, the same cells did not grow in the presence of chloramphenicol, consistent with efficient phenylselenocysteine incorporation with little to no background survival from incorporation of endogenous amino acids.

Sequencing of the candidate mutant synthetase clones revealed three different synthetase isolates, each of which is capable of functioning in an orthogonal translation system.
Clone 1 (PhSeRS-SD): Y32W, L65E, H70G, D158Q, L162S
Clone 2 (PhSeRS-K4): Y32W, L65H, H70G, F108N, Q109S, D158S, L162E
Clone 3 (PhSeRS-K5): Y32W, L65H, A67G, H70G, F108K, Q109S, D158E, L162E These clones are further summarized in the table below.

*Methanococcus jannaschii* tyrosyl-tRNA synthetase amino acid sequences Wild-Type and Mutants

|  | 32 | 65 | 67 | 70 | 108 | 109 | 158 | 162 | SEQ ID NO: |
|---|---|---|---|---|---|---|---|---|---|
| wild-type | Tyr | Leu | Ala | His | Phe | Gln | Asp | Leu | 2 |
| Mutant Clone 1 (SD) | Trp | Glu | Ala | Gly | Phe | Gln | Gln | Ser | 4 |
| Mutant Clone 2 (K4) | Trp | His | Ala | Gly | Asn | Ser | Ser | Glu | 6 |
| Mutant Clone 3 (K5) | Trp | His | Gly | Gly | Lys | Ser | Glu | Glu | 8 |

Of the three mutant synthetases isolated, the clone 2 synthetase (PhSeRS-K4) had the highest activity and specificity.

The complete nucleotide and amino acid sequences of each of these clones and the corresponding wild-type species are provided in FIG. 2.

Orthogonal Synthetase Validation

Using the mutant synthetases described herein, a myoglobin model protein containing an amber selector codon at position 4 (TAG4) was expressed in 1.5-2 mg/L yield with no background expression in the absence of phenylselenocysteine. This model protein containing phenylselenocysteine was further subjected to posttranslational modification to produce γ-carboxyglutamic acid (FIG. 1 structure 6), which was confirmed using high-resolution mass-spec.

Two additional model proteins comprising phenylselenocysteine were also expressed in 3-5 mg/L yields using the mutant synthetases and in vivo orthogonal production system described herein. Human growth hormone (hGH) was produced containing phenylselenocysteine. Following production of the phenylselenocysteine form, the protein was subject to modification to produce hGH that contains S-hexadecylcysteine. The human serum albumin binding properties and the in vivo half life of the modified hGH in mice are currently being tested.

The orthogonal reagents described herein were also used to produce green fluorescent protein (GFP) containing phenylselenocysteine. That form of the protein was also subsequently modified to form, alternatively, S-hexadecylcysteine, farnesylcysteine and palmitoylcysteine forms of GFP. The membrane-targeting properties of these lipidated forms of GFP are currently being tested.

Thus, the present invention provides compositions and methods for the genetically-programmed production of proteins containing the unnatural amino acid phenylselenocysteine (see FIG. 1, structure 1). Subsequent oxidative elimination by hydrogen peroxide produces dehydroalanine (see FIG. 1, structure 2) at the desired position. This dehydroalanine moiety can then be targeted in various secondary modification reactions.

While the foregoing invention has been described in some detail for purposes of clarity and understanding, it will be clear to one skilled in the art from a reading of this disclosure that various changes in form and detail can be made without departing from the true scope of the invention. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A translation system comprising:
   (a) a first unnatural amino acid that is phenylselenocysteine,
   (b) a first orthogonal aminoacyl-tRNA synthetase (O-RS), wherein the O-RS is at least 90% identical to SEQ ID NO: 6 and comprises: a Trp at a position corresponding to position 32 of SEQ ID NO: 6 and a Gly at a position corresponding to position 70 of SEQ ID NO:6; and, wherein the first O-RS can aminoacylate a reference tRNA comprising SEQ ID NO: 1 (MjtRNA-Tyr$_{CUA}$) with the phenylselenocysteine; and
   (c) a first orthogonal tRNA (O-tRNA), wherein the O-tRNA is at least 90% identical to SEQ ID NO: 1; and wherein the O-tRNA can be aminoacylated with the phenylselenocysteine by a reference O-RS comprising SEQ ID NO: 6; wherein said first O-RS functions to preferentially aminoacylate said first O-tRNA with said phenylselenocysteine.

2. The translation system of claim 1, wherein said first O-RS functions to preferentially aminoacylate said first O-tRNA with said phenylselenocysteine with an efficiency that is at least 50% of the efficiency of a reference aminoacyl-tRNA synthetase comprising the amino acid sequence of SEQ ID NO: 4, 6 or 8.

3. The translation system of claim 1, wherein said first O-RS comprises an amino acid sequence selected from the group consisting of amino acid sequences set forth in SEQ ID NOS: 4, 6, 8, and conservative variants thereof.

4. The translation system of claim 1, wherein said first O-tRNA is an amber suppressor tRNA.

5. The translation system of claim 1, wherein said first O-tRNA comprises the polynucleotide sequence set forth in SEQ ID NO: 1.

6. The translation system of claim 1, further comprising a nucleic acid encoding a protein of interest, said nucleic acid comprising at least one selector codon, wherein said selector codon is recognized by said first O-tRNA.

7. The translation system of claim 6, further comprising a second O-RS and a second O-tRNA, wherein the second O-RS functions to preferentially aminoacylate the second O-tRNA with a second unnatural amino acid that is different from the first unnatural amino acid, and wherein the second O-tRNA recognizes a selector codon that is different from the selector codon recognized by the first O-tRNA.

8. The translation system of claim 1, wherein said system comprises a host cell comprising said first unnatural amino acid, said first O-RS and said first O-tRNA.

9. The translation system of claim 8, wherein said host cell is a eubacterial cell.

10. The translation system of claim 9, wherein said eubacterial cell is an *E. coli* cell.

11. The translation system of claim 8, wherein said host cell comprises a polynucleotide encoding said first O-RS.

12. The translation system of claim 11, wherein said polynucleotide comprises a nucleotide sequence set forth in SEQ ID NO: 5, 7 or 9.

13. The translation system of claim 8, wherein said host cell comprises a polynucleotide encoding said first O-tRNA.

14. The translation system of claim 1, wherein the O-RS comprises: a Glu or His at a position corresponding to position 65 of SEQ ID NO: 6; an Ala or Gly at a position corresponding to position 67 of SEQ ID NO: 6; a Phe, Asn or Lys at a position corresponding to position 108 of SEQ ID NO: 6; a Gln or Ser at a position corresponding to position 109 of SEQ ID NO: 6; a GLN, Ser or Glu at a position corresponding to position 158 of SEQ ID NO: 6; or a Ser or Glu at a position corresponding to position 162 of SEQ ID NO: 6.

15. The translation system of claim 14, wherein the O-RS is at least 95% identical to SEQ ID NO: 6.

16. The translation system of claim 1, wherein the O-RS comprises: a Trp at a position corresponding to position 32 of SEQ ID NO: 6; a Glu or His at a position corresponding to position 65 of SEQ ID NO: 6; an Ala or Gly at a position corresponding to position 67 of SEQ ID NO: 6; a Gly at a position corresponding to position 70 of SEQ ID NO: 6; a Phe, Asn or Lys at a position corresponding to position 108 of SEQ ID NO: 6; a Gln or Ser at a position corresponding to position 109 of SEQ ID NO: 6; a GLN, Ser or Glu at a position corresponding to position 158 of SEQ ID NO: 6; and a Ser or Glu at a position corresponding to position 162 of SEQ ID NO: 6.

* * * * *

UNITED STATES PATENT AND TRADEMARK OFFICE
CERTIFICATE OF CORRECTION

| | | |
|---|---|---|
| PATENT NO. | : 7,790,847 B2 | Page 1 of 1 |
| APPLICATION NO. | : 11/724039 | |
| DATED | : September 7, 2010 | |
| INVENTOR(S) | : Wang et al. | |

It is certified that error appears in the above-identified patent and that said Letters Patent is hereby corrected as shown below:

In the Specification

Column 1, Lines 15-23, the paragraph STATEMENT AS TO RIGHT TO INVENTIONS MADE UNDER FEDERALLY SPONSORED RESEARCH AND DEVELOPMENT should be changed to:
-- STATEMENT OF GOVERNMENT LICENSE RIGHTS
This invention was made with government support under grant number GM062159 awarded by the National Institutes of Health and under grant numbers DE-FG02-03ER46051 and DE-FG03-00ER45812 awarded by the United States Department of Energy. The government has certain rights in the invention. --

Signed and Sealed this
Twenty-first Day of April, 2020

Andrei Iancu
*Director of the United States Patent and Trademark Office*

SEQUENCE LISTING

<160> NUMBER OF SEQ ID NOS: 9

<210> SEQ ID NO 1
<211> LENGTH: 77
<212> TYPE: RNA
<213> ORGANISM: Artificial
<220> FEATURE:
<223> OTHER INFORMATION: nonsense suppressor tyrosyl-tRNA CUA derived
      from Methanococcus jannaschii

<400> SEQUENCE: 1
ccggcgguag uucagcaggg cagaacggcg gacucuaaau ccgcauggcg cugguucaaa      60
uccggcccgc cggacca                                                              77

<210> SEQ ID NO 2
<211> LENGTH: 306
<212> TYPE: PRT
<213> ORGANISM: Methanococcus jannaschii

<400> SEQUENCE: 2

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 3
<211> LENGTH: 918
<212> TYPE: DNA
<213> ORGANISM: Methanococcus jannaschii

<400> SEQUENCE: 3
atggacgaat tgaaatgat aaagagaaac acatctgaaa ttatcagcga ggaagagtta    60

-continued

```
agagaggttt taaaaaaaga tgaaaaatct gcttacatag gttttgaacc aagtggtaaa    120
atacatttag ggcattatct ccaaataaaa aagatgattg atttacaaaa tgctggattt    180
gatataatta tattgttggc tgatttacac gcctatttaa accagaaagg agagttggat    240
gagattagaa aataggaga ttataacaaa aaagttttg aagcaatggg gttaaaggca      300
aaatatgttt atggaagtga attccagctt gataaggatt atacactgaa tgtctataga    360
ttggctttaa aaactacctt aaaaagagca agaaggagta tggaacttat agcaagagag    420
gatgaaaatc caaggttgc tgaagttatc tatccaataa tgcaggttaa tgatattcat      480
tatttaggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaagggg aattttatag ctgttgatga ctctccagaa    660
gagattaggg ctaagataaa gaaagcatac tgcccagctg gagttgttga aggaaatcca    720
ataatggaga tagctaaata cttccttgaa tatccttttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagatta                                                   918
```

<210> SEQ ID NO 4
<211> LENGTH: 306
<212> TYPE: PRT
<213> ORGANISM: Artificial
<220> FEATURE:
<223> OTHER INFORMATION: Phenylselenocysteine aminoacyl tRNA synthetase

<400> SEQUENCE: 4

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Trp
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Glu Leu Ala Asp Leu Gly Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gln Ile His
145                 150                 155                 160

Tyr Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205
```

```
Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 5
<211> LENGTH: 921
<212> TYPE: DNA
<213> ORGANISM: Artificial
<220> FEATURE:
<223> OTHER INFORMATION: Phenylselenocysteine aminoacyl tRNA synthetase

<400> SEQUENCE: 5
atggacgaat tgaaatgat aaagagaaac acatctgaaa ttatcagcga ggaagagtta      60
agagaggttt taaaaaaaga tgaaaaatct gcttggatag gttttgaacc aagtggtaaa    120
atacatttag gcattatct ccaaataaaa aagatgattg atttacaaaa tgctggattt    180
gatataatta tagagttggc tgatttaggg gcctatttaa accagaaagg agagttggat    240
gagattagaa aaataggaga ttataacaaa aaagttttg aagcaatggg gttaaaggca    300
aaatatgttt atggaagtga attccagctt gataaggatt atacactgaa tgtctataga    360
ttggctttaa aaactacctt aaaaagagca agaaggagta tggaacttat agcaagagag    420
gatgaaaatc caaggttgc tgaagttatc tatccaataa tgcaggttaa tcaaattcat    480
tatagtggcg ttgatgttgc agttggaggg atggagcaga aaaaatatca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatccttta ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                             921

<210> SEQ ID NO 6
<211> LENGTH: 306
<212> TYPE: PRT
<213> ORGANISM: Artificial
<220> FEATURE:
<223> OTHER INFORMATION: Phenylselenocysteine aminoacyl tRNA synthetase

<400> SEQUENCE: 6

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Trp
            20                  25                  30
```

```
Ile Gly Phe Glu Pro Ser Gly Lys Ile His Leu Gly His Tyr Leu Gln
            35                  40                  45
Ile Lys Lys Met Ile Asp Leu Gln Asn Ala Gly Phe Asp Ile Ile Ile
 50                  55                  60
His Leu Ala Asp Leu Gly Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Glu Asn Ser Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Ser Ile His
145                 150                 155                 160
Tyr Glu Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
            180                 185                 190
Asn Pro Val Leu Thr Gly Leu Asp Gly Glu Gly Lys Met Ser Ser Ser
        195                 200                 205
Lys Gly Asn Phe Ile Ala Val Asp Asp Ser Pro Glu Glu Ile Arg Ala
    210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
            260                 265                 270
Leu Glu Ser Leu Phe Lys Asn Lys Glu Leu His Pro Met Asp Leu Lys
        275                 280                 285
Asn Ala Val Ala Glu Glu Leu Ile Lys Ile Leu Glu Pro Ile Arg Lys
    290                 295                 300
Arg Leu
305

<210> SEQ ID NO 7
<211> LENGTH: 921
<212> TYPE: DNA
<213> ORGANISM: Artificial
<220> FEATURE:
<223> OTHER INFORMATION: Phenylselenocysteine aminoacyl tRNA synthetase

<400> SEQUENCE: 7
atggacgaat ttgaaatgat aaagagaaac acatctgaaa ttatcagcga ggaagagtta      60
agagaggttt taaaaaaaga tgaaaaatct gcttggatag gttttgaacc aagtggtaaa     120
atacatttag gcattatctc ccaaataaaa aagatgattg atttacaaaa tgctggattt     180
gatataatta cacatttggc tgatttaggc gcctatttaa accagaaagg agagttggat     240
gagattagaa aaataggaga ttataacaaa aaagttttg aagcaatggg gttaaaggca     300
aaatatgttt atggaagtga aaattctctt gataaggatt atacactgaa tgtctataga     360
ttggctttaa aaactacctt aaaaagagca agaaggagta tggaacttat agcaagagag     420
```

-continued

```
gatgaaaatc caaaggttgc tgaagttatc tatccaataa tgcaggttaa ttctattcat    480
tatgagggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatgagaa tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                              921
```

<210> SEQ ID NO 8
<211> LENGTH: 306
<212> TYPE: PRT
<213> ORGANISM: Artificial
<220> FEATURE:
<223> OTHER INFORMATION: Phenylselenocysteine aminoacyl tRNA synthetase

<400> SEQUENCE: 8

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Trp
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

His Leu Gly Asp Leu Gly Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Lys Ser Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Glu Ile His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270
```

-continued

```
Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 9
<211> LENGTH: 921
<212> TYPE: DNA
<213> ORGANISM: Artificial
<220> FEATURE:
<223> OTHER INFORMATION: Phenylselenocysteine aminoacyl tRNA synthetase

<400> SEQUENCE: 9
atggacgaat ttgaaatgat aaagagaaac acatctgaaa ttatcagcga ggaagagtta      60
agagaggttt taaaaaaaga tgaaaaatct gcttggatag gttttgaacc aagtggtaaa     120
atacatttag ggcattatct ccaaataaaa aagatgattg atttacaaaa tgctggattt     180
gatataatta tacatttggg tgatttaggc gcctatttaa accagaaagg agagttggat     240
gagattagaa aaataggaga ttataacaaa aaagtttttg aagcaatggg gttaaaggca     300
aaatatgttt atggaagtga aaagtctctt gataaggatt atacactgaa tgtctataga     360
ttggctttaa aaactacctt aaaaagagca agaaggagta tggaacttat agcaagagag     420
gatgaaaatc caaaggttgc tgaagttatc tatccaataa tgcaggttaa tgagattcat     480
tatgagggcg ttgatgttgc agttggaggg atggagcaga gaaaaataca catgttagca     540
agggagcttt taccaaaaaa ggttgtttgt attcacaacc ctgtcttaac gggtttggat     600
ggagaaggaa agatgagttc ttcaaaaggg aattttatag ctgttgatga ctctccagaa     660
gagattaggg ctaagataaa gaaagcatac tgcccagctg gagttgttga aggaaatcca     720
ataatggaga tagctaaata cttccttgaa tatcctttaa ccataaaaag gccagaaaaa     780
tttggtggag atttgacagt taatagctat gaggagttag agagtttatt taaaaataag     840
gaattgcatc caatggattt aaaaaatgct gtagctgaag aacttataaa gattttagag     900
ccaattagaa agagattata a                                               921
```